United States Patent
Nishino

(10) Patent No.: US 8,517,919 B2
(45) Date of Patent: Aug. 27, 2013

(54) CAPSULE ENDOSCOPIC SYSTEM AND OPERATION CONTROL METHOD OF CAPSULE ENDOSCOPE

(75) Inventor: Naoyuki Nishino, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1515 days.

(21) Appl. No.: 12/043,523

(22) Filed: Mar. 6, 2008

(65) Prior Publication Data
US 2008/0242931 A1 Oct. 2, 2008

(30) Foreign Application Priority Data

Mar. 28, 2007 (JP) ................................. 2007-083456

(51) Int. Cl.
*A61B 1/00* (2006.01)
*A61B 1/04* (2006.01)
*A61B 1/06* (2006.01)

(52) U.S. Cl.
USPC ........... 600/118; 600/103; 600/109; 600/117; 600/160

(58) Field of Classification Search
USPC ............... 600/101, 109, 117, 118, 361, 424, 600/103, 160, 178; 348/45, 65, 399.1
See application file for complete search history.

(56) References Cited

U.S. PATENT DOCUMENTS

| | | | |
|---|---|---|---|
| 2002/0158875 A1* | 10/2002 | Yamada | 345/440 |
| 2003/0020810 A1* | 1/2003 | Takizawa et al. | 348/68 |
| 2004/0073087 A1* | 4/2004 | Glukhovsky et al. | 600/109 |
| 2004/0111011 A1* | 6/2004 | Uchiyama et al. | 600/160 |
| 2005/0054897 A1* | 3/2005 | Hashimoto et al. | 600/118 |
| 2005/0250991 A1* | 11/2005 | Mizuno | 600/160 |
| 2007/0191677 A1* | 8/2007 | Nishimura et al. | 600/109 |

FOREIGN PATENT DOCUMENTS

| | | |
|---|---|---|
| JP | 2004-521662 A | 7/2004 |
| JP | 2004-350963 A | 12/2004 |
| JP | 2005-193066 A | 7/2005 |
| JP | 2006-223892 A | 8/2006 |
| JP | 2006-288808 A | 10/2006 |

* cited by examiner

*Primary Examiner* — Philip R Smith
*Assistant Examiner* — Rynae Boler
(74) *Attorney, Agent, or Firm* — Sughrue Mion, PLLC

(57) ABSTRACT

A receiver of capsule endoscopic system downloads diagnostic information of a patient obtained by a past diagnosis from a data storage of work station. A data analyzer of the receiver compares the diagnostic information and present information obtained by use of a capsule endoscope during endoscopy. A CPU produces a control command in which a frame rate of image shooting by use of the capsule endoscope is set based on an analysis result of the data analyzer. The produced control command is wirelessly transmitted via a radio wave from the receiver. The capsule endoscope wirelessly receives the control command from the receiver via the radio wave, and performs image shooting with the frame rate set by the control command.

22 Claims, 14 Drawing Sheets

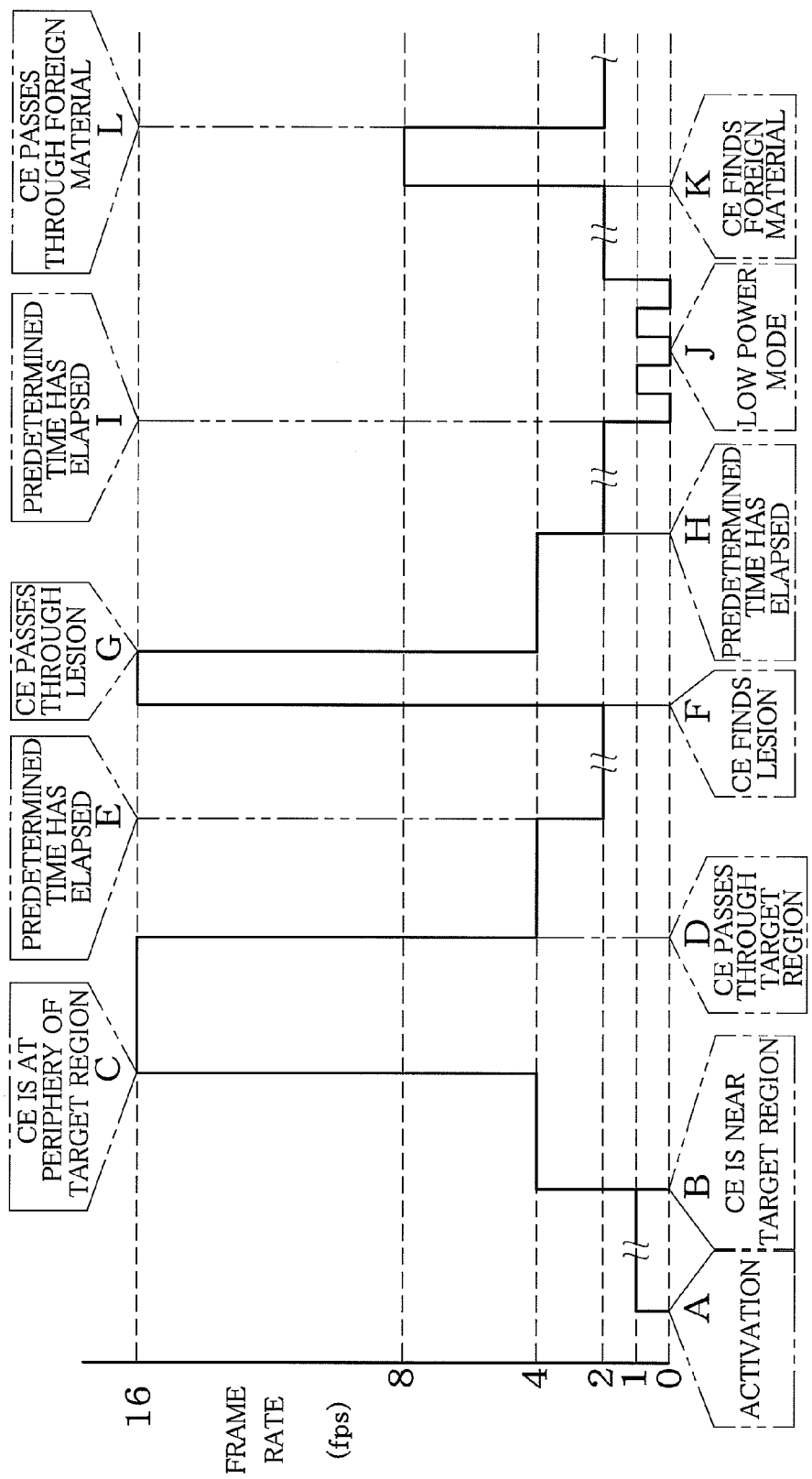

FIG.19

| PURPOSE | COMMAND | INDEX NO. | COMPONENT NAME | EXPLANATION |
|---|---|---|---|---|
| POWER SOURCE SYSTEM | 00 | | Reset | RESETTING SYSTEM |
| | 01 | | Wake-Up | RETURN FROM Deep Sleep OR Sleep |
| | 02 | | Deep Sleep | WITHOUT BEACON SIGNAL |
| | 03 | | Sleep | WITH BEACON SIGNAL |
| IMAGING SYSTEM | 10(n) | 1, 2 | Mode | 1: CONSECUTIVE  2: ONE SHOT |
| | 11(n) | 1-32 | FRAME RATE | n/2(fps) |
| | 15 | | RELEASE | ONE-SHOT IMAGING |
| LIGHT SYSTEM | 20(n) | 1-4 | KIND OF LIGHT SOURCES | 1: SHORT-RANGE  2: LONG-RANGE  3: BOTH SHRT-RANGE AND LONG-RANGE  4: NON-WHITE |
| | 21(n) | 2, 4 | NUMBER OF LIGHT SOURCES TO BE LIGHTENED | |
| | 22(n) | 0-255 | LIGHT AMOUNT | 0.1×n(mA) |
| | 23(n) | 0-255 | LIGHTENING TIME | 0.1×n(mSec) |
| PRESET | 30 | | CONDITION 0 | CLOSE-UP/ FRAME RATE: 16Fps  LIGHT: 4 SHORT-RANGE |
| | 31 | | CONDITION 1 | STANDBY/ FRAME RATE: 4Fps  LIGHT: 4 SHORT-RANGE AND 2 LONG-RANGE |
| | 32 | | CONDITION 2 | NORMAL/ FRAME RATE: 0.5Fps  LIGHT: 2 SHORT-RANGE AND 2 LONG-RANGE |
| OTHERS | 40 | | CONTINUATION | NO CHANGE IN CONDITION |
| | 41(n) | 1-16 | TRANSMISSION POWER | $P = n/16 \times P_{max}$    $P_{max}$ AS MAXIMUM NOT OVER STANDARD POWER |

CAPSULE ENDOSCOPIC SYSTEM AND OPERATION CONTROL METHOD OF CAPSULE ENDOSCOPE

FIELD OF THE INVENTION

The present invention relates to a capsule endoscopic system in which an image inside a body of a patient obtained by a capsule endoscope is used for medical diagnosis, and an operation control method of the capsule endoscope.

BACKGROUND OF THE INVENTION

Recently, medical diagnosis by use of a capsule endoscope incorporating an image sensor, a light source, and the like in an extremely small capsule has been put to practical use. In the medical diagnosis by use of the capsule endoscope, at first, the capsule endoscope is swallowed by a patient, and while a region to be observed inside a body of a patient (inner wall surface of tracts in the human body) is illuminated by the light source, the region to be observed is shot by the image sensor. Image data thus obtained is wirelessly transmitted to a receiver, and sequentially stored in a recording medium such as a flash memory provided in the receiver. During or after the endoscopy, the image data is retrieved to an information management device such as a work station, and then the image is displayed on the monitor and read for diagnosis.

Number of shooting images by the capsule endoscope per unit time (frame rate) is 2 fps (frame/second), for example. The image shooting is performed for at least eight hours, and the amount of image data stored in the receiver is huge. Therefore, in a case where the image is read out for diagnosis after the endoscopy, when all the shot images are to be read out, it takes a lot of time and work. Conventionally, in order to reduce the burden in the image reading, there are various propositions (for example, see Japanese Patent Translation Publication No. 2004-521662, Japanese Patent Application Laid-open Publication No. 2006-223892, and Japanese Patent Application Laid-open Publication No. 2006-288808).

According to the inventions disclosed in the Japanese Patent Translation Publication No. 2004-521662 and the Japanese Patent Application Laid-open Publication No. 2006-223892, an acceleration sensor and a pressure sensor are used to detect the moving speed of the capsule endoscope in the human body. The frame rate is raised when the moving speed is fast, and the frame rate is lowered when the moving speed is slow. According to the invention disclosed in the Japanese Patent Application Laid-open Publication No. 2006-288808, the strength of a wireless signal transmitted/received between the capsule endoscope and the receiver is detected, and based on the detection result, the position of the capsule endoscope, and then its moving distance are detected. If the moving distance is equal to or less than a threshold value, the operation of the image sensor is halted.

In a case where the moving speed of the capsule endoscope is slow, or the moving distance thereof is equal to or less than a threshold value, there is a possibility that the capsule endoscope remains at the same spot for a long time, and in this case, plural similar images are shot. Accordingly, as disclosed in the Japanese Patent Translation Publication No. 2004-521662 and the Japanese Patent Application Laid-open Publication No. 2006-223892, the frame rate is lowered, or as disclosed in the Japanese Patent Application Laid-open Publication No. 2006-288808, the operation of the image sensor is halted. Thereby, the number of similar images can be decreased, and the burden in the image reading also can be decreased.

While there is a demand for decreasing burden in the image reading as descried above, there is a demand for minutely reading an image of a region to be diagnosed intensively (hereinafter referred to as target region) such as a lesion. Namely, it is expected that the images unnecessary for diagnosis are decreased and the images necessary for diagnosis are increased as much as possible. In view of the above, there is proposed a capsule endoscope capable of shooting images in accordance with a preset time schedule (see Japanese Patent Application Laid-open Publication No. 2005-193066).

In accordance with the Japanese Patent Application Laid-open Publication No. 2005-193066, for example, the time required for the capsule endoscope to pass through an esophagus is as short as within one second in general, and therefore the frame rate is raised when the capsule endoscope is passing through the esophagus. When the capsule endoscope falls into a stomach, the image shooting operation is halted in accordance with the time schedule set previously. Alternatively, when the capsule endoscope is passing through the target region, the frame rate is raised, and after the capsule endoscope has passed through the target region, the frame rate is lowered.

Moreover, there is proposed a capsule endoscope incorporating a memory for storing a parameter for setting the operation condition of each component of the capsule endoscope in which the data stored in the memory can be rewritten wirelessly from the receiver (see Japanese Patent Application Laid-open Publication No. 2004-350963). According to the Japanese Patent Application Laid-open Publication No. 2004-350963, the data stored in the memory is written to correct each of the light amount of the light source and white balance to achieve an appropriate level, and the light amount is changed at each region. Moreover, as in the case of the Japanese Patent Application Laid-open Publication No. 2005-193066, there is described an example that when the capsule endoscope is near the target region, the frame rate is raised, and when the capsule endoscope is away from the target region, the frame rate is lowered.

The diagnosis by use of the capsule endoscope has an advantage (low invasiveness) in that the patient has burden less than that by use of a conventional insertion-type endoscope. Therefore, there is a possibility that the capsule endoscope is used more widely for routine medical examination and past-surgery inspection in the near future. Accordingly, a demand for reading an image of the target region requiring observation, such as a lesion found in the last routine medical examination and a surgery site, more in detail for a short time has been increasing.

However, according to the inventions disclosed in the Japanese Patent Translation Publication No. 2004-521662, the Japanese Patent Application Laid-open Publication No. 2006-223892, and the Japanese Patent Application Laid-open Publication No. 2006-288808, although it is possible to reduce the burden in the image reading, if the moving speed of the capsule endoscope is slow or if the moving distance thereof is equal to or less than the threshold value, when the capsule endoscope is in the target region, the image shooting of the target region is omitted. Therefore, there is a fear that it becomes impossible to read an image of the target region in detail.

Moreover, according to the inventions disclosed in the Japanese Patent Application Laid-open Publication No. 2005-193066 and the Japanese Patent Application Laid-open Publication No. 2004-350963, the frame rate is raised when the capsule endoscope is passing through the target region, and the frame rate is lowered after the capsule endoscope has passed through the target region. However, there is disclosed no examples for specifying the target region. Therefore, as in the case of the Japanese Patent Translation Publication No. 2004-521662, the Japanese Patent Application Laid-open Publication No. 2006-223892, and the Japanese Patent Application Laid-open Publication No. 2006-288808, the demand for reading images of the target region more in detail in a short time can not be achieved.

SUMMARY OF THE INVENTION

In view of the above, an object of the present invention is to provide a capsule endoscopic system capable of reading an image of a target region more in detail in a short time, and to provide an operation control method of this capsule endoscope.

To achieve the above and other objects, according to the present invention, there is provided a capsule endoscopic system including: a capsule endoscope swallowed by a patient to be inspected for shooting an image of a region to be observed inside a body of the patient; a receiver for wirelessly receiving image data of the region to be observed obtained by the capsule endoscope and storing the image data; and an information management device for retrieving the image data of the region to be observed from the receiver to store and manage the image data. The information management device includes a first storage device for storing past diagnostic information of the patient. The receiver includes a second storage device for storing the diagnostic information retrieved from the information management device, a first data analyzer for comparing the diagnostic information and present information obtained by the capsule endoscope during endoscopy, a control command producer for producing a control command to control operation of each component of the capsule endoscope based on an analysis result of the first data analyzer, and a wireless transmitter for wirelessly transmitting the control command. The capsule endoscope includes a wireless receiver for wirelessly receiving the control command and an operation controller for causing each component of the capsule endoscope to operate in accordance with the control command.

The control command preferably specifies a frame rate of the image shooting.

Preferably, the control command is a release signal for performing the image shooting.

The control command preferably switches the capsule endoscope between a first operation mode for performing the image shooting at a fixed timing and a second operation mode for performing the image shooting at an arbitrary timing. In this case, the image shooting is performed first and then the control command is produced based on image data obtained by the image shooting in the first operation mode, and the control command is produced first and then the image shooting is performed in accordance with the control command in the second operation mode.

The control command preferably switches the capsule endoscope to a third operation mode in which the image shooting is halted.

The control command preferably specifies a driving condition of a light source section in the capsule endoscope. In this case, the driving condition includes at least one of a kind of light sources constituting the light source section, a number of the light sources to be lightened, a light amount, and a lightening time.

The diagnostic information preferably includes image data at a periphery of a target region inside the body of the patient to be inspected. Further, the diagnostic information prefer- ably includes position information at a periphery of the target region inside the body of the patient.

Preferably, the position information is stored in relation with the image data of the region to be observed.

The position information preferably includes at least one of a position of the capsule endoscope at the time of shooting an image at a periphery of the target region, operation time of the capsule endoscope, and a moving distance of the capsule endoscope.

The capsule endoscopic system further includes at least one of a position detector for detecting a position of the capsule endoscope, an operation time measurement device for measuring operation time of the capsule endoscope, and a moving distance measurement device for measuring a moving distance of the capsule endoscope. Preferably, at least one of a detection result of the position detector, a measurement result of the operation time measurement device, and a measurement result of the moving distance measurement device is used as the position information.

The position detector includes an electric field strength detector for detecting an electric filed strength of a wireless signal transmitted/received between the capsule endoscope and the receiver.

The operation time measurement device includes a clock circuit incorporated in the capsule endoscope or the receiver.

The moving distance measurement device includes an acceleration sensor for measuring acceleration of the capsule endoscope and an integrator for integrating the measurement result of the acceleration sensor.

The capsule endoscopic system further includes a pylorus passage detector for detecting that the capsule endoscope passes through a pylorus. A point of time when the pylorus passage detector detects that the capsule endoscope passes through the pylorus is preferably considered as a reference point of the operation time and the moving distance of the capsule endoscope. In this case, the pylorus passage detector includes a pH sensor for measuring pH inside the body of the patient to be inspected.

The information management device includes a third storage device for storing case information obtained from a typical instance of disease. The receiver includes a fourth storage device for storing the case information retrieved from the information management device, and a second data analyzer for comparing the case information and the present information. The control command producer produces the control command based on an analysis result of the second data analyzer. In this case, the case information includes image data of at least one of a typical lesion and a foreign substance.

The capsule endoscope preferably includes a fifth storage device for storing an operation condition of each component of the capsule endoscope set by the control command. Further, the wireless transmitter and the wireless receiver are used to wirelessly transmit/receive the image data of the region to be observed.

Moreover, according to the present invention, there is provided an operation control method of capsule endoscope including the steps of: retrieving past diagnostic information of a patient to be inspected from an information management device to a receiver; comparing and analyzing the diagnostic information and present information obtained by a capsule endoscope during endoscopy; producing a control command to control operation of each component of the capsule endoscope based on an analysis result of the analyzing step; wirelessly transmitting and receiving the control command between the receiver and the capsule endoscope; and causing each component of the capsule endoscope to operate in accordance with the control command.

According to the capsule endoscopic system and the operation control method of the capsule endoscope of the present invention, based on the comparison result between the past diagnostic information and the present information obtained by the capsule endoscope during the endoscopy, the operation of each component of the capsule endoscope is controlled. Therefore, if the image of the target region and the position information are prepared as the diagnostic information, the target region can be identified in comparison with the present information. This enables controlling the capsule endoscope such that, for example, when the capsule endoscope is passing through the target region, the frame rate can be raised, and after the capsule endoscope has passed through the target region, the frame rate can be lowered. As a result, it is possible to reading images of the target region more in detail in a short time.

BRIEF DESCRIPTION OF THE DRAWINGS

One with ordinary skill in the art would easily understand the above-described objects and advantages of the present invention when the following detailed description is read with reference to the drawings attached hereto:

FIG. 18 is an explanatory view showing an example of transition of frame rate; and FIG. 19 is an explanatory view showing an example of a control command.

DESCRIPTION OF THE PREFERRED EMBODIMENTS

Embodiments of the present invention are described hereinbelow. The present invention, however, is not limited to the following embodiments.

Figure 1:
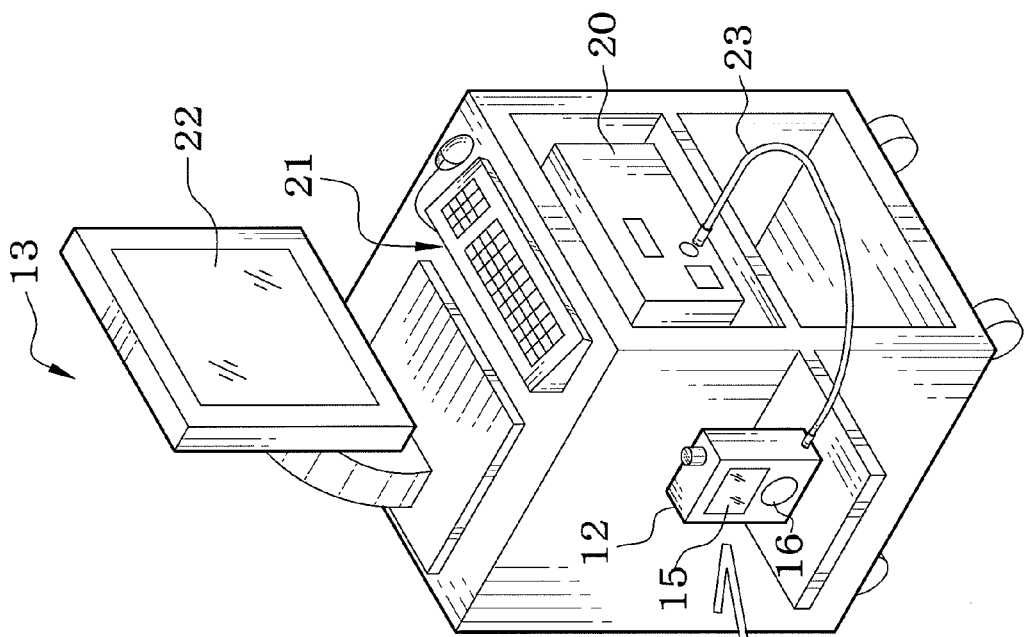
FIG. 1 is a schematic diagram illustrating a configuration of a capsule endoscopic system according to an embodiment of the present invention.
Figure 1:
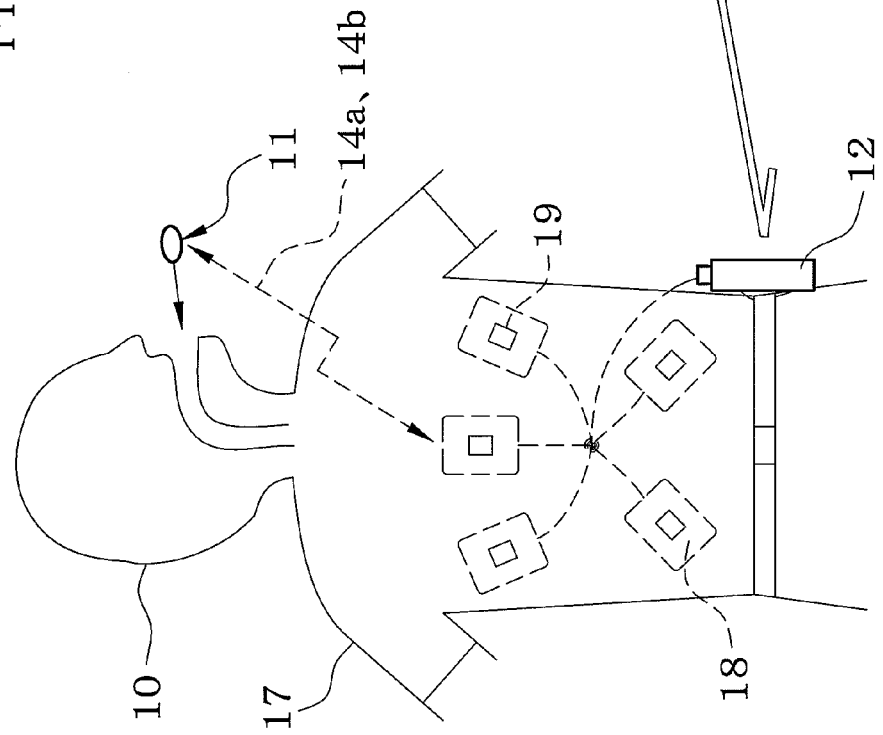

As shown in FIG. 1, a capsule endoscopic system includes a capsule endoscope (hereinafter abbreviated as CE) 11, a receiver 12, and a work station (hereinafter abbreviated as WS) 13. The capsule endoscope 11 is taken into a body through a mouth of a patient 10. The receiver 12 is attached to a belt of the patient 10. A doctor uses the WS 13 to read an image obtained by the CE 11 for diagnosis.

While passing through tracts in the human body, the CE 11 shoots images of inner wall surface of the tracts. The obtained image data is wirelessly transmitted to the receiver 12 via a radio wave 14a. Further, the CE 11 wirelessly receives a control command from the receiver 12 via a radio wave 14b, and operates in accordance with the control command.

The receiver 12 includes a liquid crystal display (hereinafter abbreviated as LCD) 15 for displaying various setting screens, and an input panel 16 for performing various settings. The receiver 12 wirelessly receives and stores image data wirelessly transmitted from the CE 11 via the radio wave 14a. Further, the receiver 12 produces the control command based on diagnostic information of the patient 10 obtained by a past capsule endoscopy and the like, and wirelessly transmits the control command to the CE 11 via the radio wave 14b. Namely, the CE 11 functions as a slave operated by the control command, and the receiver 12 functions as a master for giving a command to the CE 11 by the control command.

The radio waves 14a and 14b are transmitted/received between the CE 11 and the receiver 12 through an antenna 39 (see FIGS. 2 and 3) provided in the CE 11 and plural antennas 18 attached to a shield shirt 17 worn by the patient 10. The antenna 18 incorporates an electric field strength detector 19 for detecting electric field strength of the radio wave 14a transmitted from the CE 11. The electric field strength detector 19 outputs a detection result of the electric field strength to a position detector 79 (see FIG. 4).

The WS 13 includes a processor 20, a user interface 21 such as a key board and a mouse, and a monitor 22. The processor 20 is connected to the receiver 12 through a universal serial bus (USB) cable 23 (alternatively, wireless communication such as infrared communication), for example, and exchanges the data with the receiver 12. The processor 20 retrieves the image data from the receiver 12 during or after the endoscopy using the CE 11, and stores/manages the image data for each patient. Further, the processor 20 transmits the diagnostic information to the receiver 12 before the endoscopy. Moreover, the processor 20 produces an image for displaying from the image data, and displays the image on the monitor 22.

Figure 2:
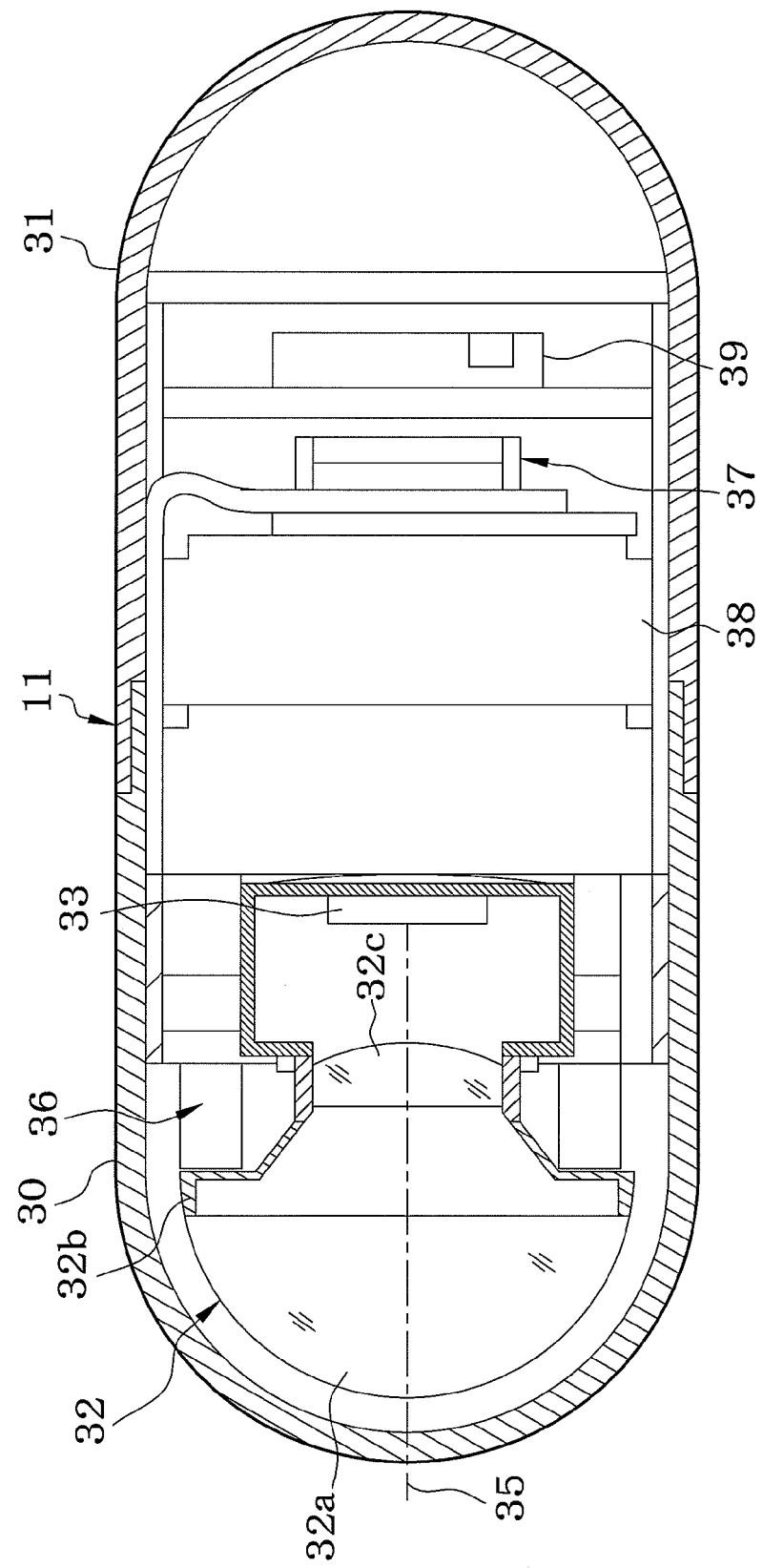
FIG. 2 is a cross sectional view illustrating an internal configuration of a capsule endoscope.

As shown in FIG. 2, the CE 11 includes a transparent front cover 30 and a rear cover 31 fitted into the front cover 30 to form water-tight space. Each of the front cover 30 and the rear cover 31 has a tubular-shape whose front end or rear end is almost hemispheric.

The space formed by the front cover 30 and the rear cover 31 contains an image pickup section including an objective optical system 32 for collecting image light of a region to be observed and an image sensor 33 such as charge-coupled device (CCD) or complementary metal-oxide semiconductor (CMOS) for shooting the image of the region to be observed.

The image light of the region to be observed entering through the objective optical system 32 is focused on a pickup surface of the image sensor 33. The image sensor 33 outputs a pickup signal of each pixel.

The objective optical system 32 includes a transparent convex optical dome 32a attached to the almost hemispherical front end of the front cover 30, a lens holder 32b narrowed toward its rear end and attached to the rear end of the optical dome 32a, and a lens 32c fixed to the lens holder 32b. The objective optical system 32 covers an imaging field with front viewing angle of 140° to 180°, for example, around an optical axis 35, and collects the image light of omnidirectional image of the region to be observed in the imaging field.

Inside the front cover 30 and the rear cover 31 there are contained not only the image pickup section but also an light source section 36 for emitting light toward the region to be observed, an electrical circuit board 37 onto which a transmitting/receiving circuit 55 and power source 58 (see FIG. 3) are mounted, a button cell battery 38, the antenna 39 for transmitting/receiving the radio waves 14a and 14b, and the like.

Figure 3:
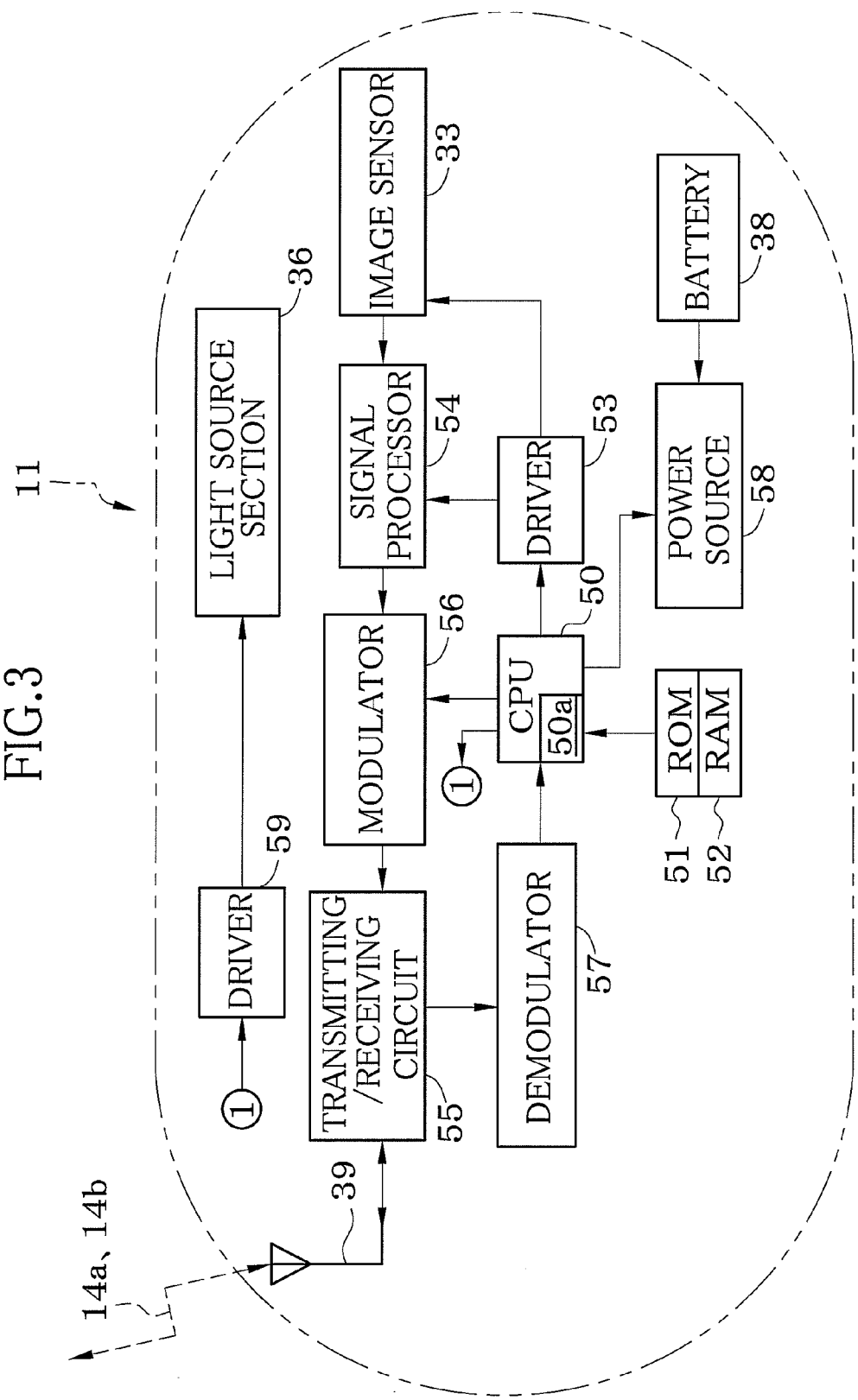
FIG. 3 is a block diagram illustrating an electrical configuration of the capsule endoscope.

As shown in FIG. 3, a CPU 50 controls all the operation of the CE 11 as a whole. A read-only memory (ROM) 51 and a random access memory (RAM) 52 are connected to the CPU 50. Various programs and data for controlling the operation of the CE 11 are stored in the ROM 51. The CPU 50 retrieves necessary programs and data from ROM 51 and expands the programs and data to the RAM 52 to sequentially process the retrieved programs. The RAM 52 also temporarily stores the data of frame rate set by the control command from the receiver 12.

A driver 53 and a signal processor 54 are connected to the image sensor 33. The driver 53 controls the operation of the image sensor 33 and the signal processor 54 such that image shooting is performed with the frame rate set by the control command. The signal processor 54 subjects the pickup signal outputted from the image sensor 33 to related double sampling, amplification, and A/D conversion, and thereby converts the pickup signal to the digital image data. Then, the signal processor 54 subjects the converted image data to various kinds of image processing such as γ conversion.

The transmitting/receiving circuit 55 is connected to the antenna 39. A modulator 56 and a demodulator 57 are connected to the transmitting/receiving circuit 55, and further connected to the CPU 50. The modulator 56 modulates the digital image data outputted from the signal processor 54 to the radio wave 14a, and outputs the modulated radio wave 14a to transmitting/receiving circuit 55. The demodulator 57 demodulates the radio wave 14b from the receiver 12 to the original control command, and outputs the demodulated control command to the CPU 50. The transmitting/receiving circuit 55 subjects the radio wave 14a from the modulator 56 to amplification and band-pass filtering, and then outputs the radio wave 14a to the antenna 39. Further, the transmitting/receiving circuit 55 subjects the radio wave 14b received by the antenna 39 to amplification and band-pass filtering, and then outputs the radio wave 14b to the demodulator 57.

The power source 58 supplies the electric power of the battery 38 to respective components of the CE 11. Note that reference numeral 59 denotes a driver for controlling the operation of the light source section 36 under the control of the CPU 50.

Figure 4:
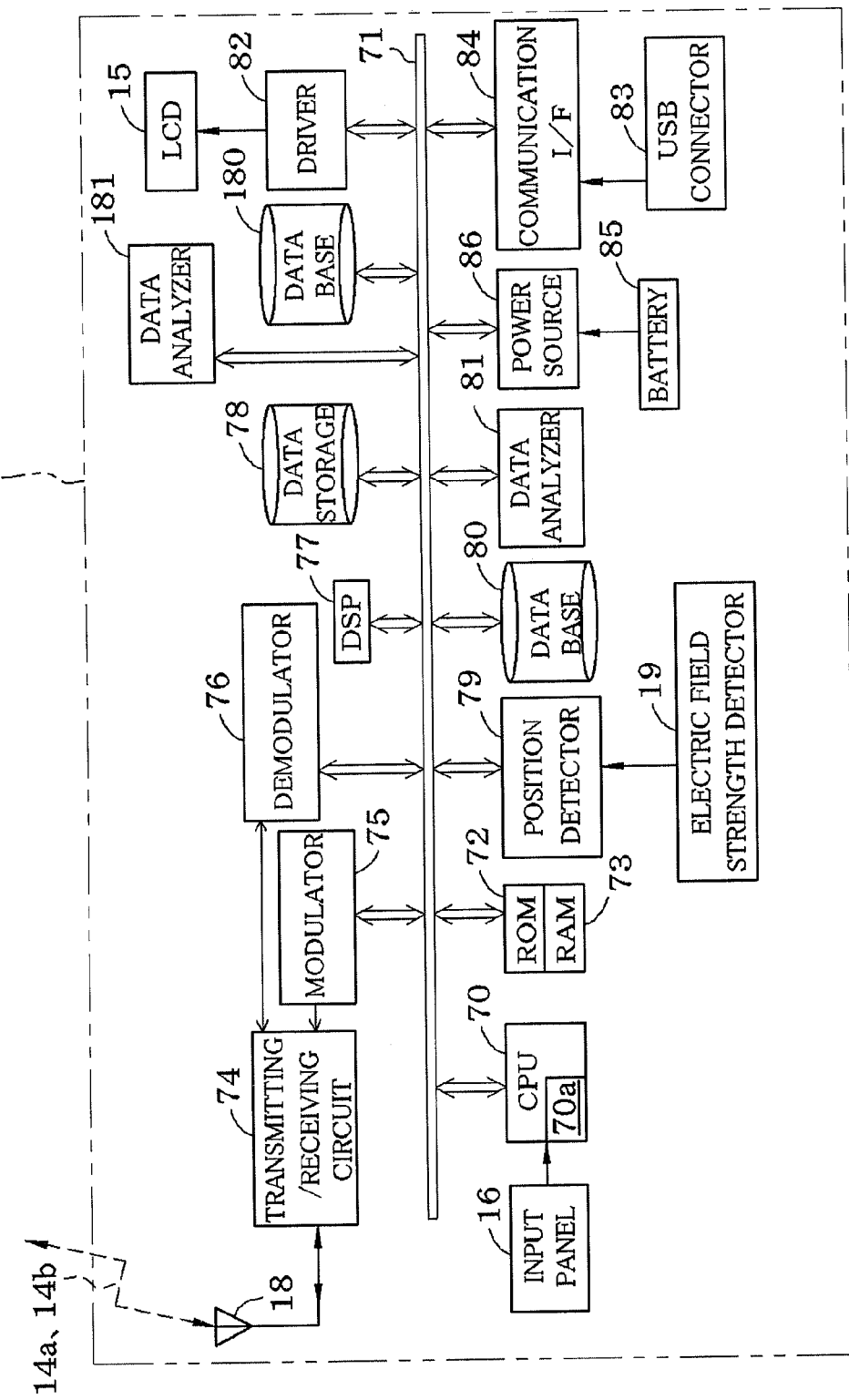
FIG. 4 is a block diagram illustrating an electrical configuration of a receiver.

As shown in FIG. 4, a CPU 70 controls all the operation of the receiver 12 as a whole. A read-only memory (ROM) 72 and a random access memory (RAM) 73 are connected to the CPU 70 via a bus 71. Various programs and data for controlling the operation of the receiver 12 are stored in the ROM 72. The CPU 70 retrieves necessary programs and data from ROM 72 and expands the programs and data to the RAM 73 to sequentially process the retrieved programs. Further, the CPU 70 causes each component of the receiver 12 to operate in accordance with the operation input signal from the input panel 16.

A transmitting/receiving circuit 74 is connected to the antenna 18. A modulator 75 and a demodulator 76 are connected to the transmitting/receiving circuit 74. The modulator 75 modulates the control command to the radio wave 14b, and outputs the modulated radio wave 14b to the transmitting/receiving circuit 74. The demodulator 76 demodulates the radio wave 14a from the CE 11 to the original image data, and outputs the demodulated image data to a digital signal processor (DSP) 77. The transmitting/receiving circuit 74 subjects the radio wave 14b from the modulator 75 to amplification and band-pass filtering, and then outputs the radio wave 14b to the antenna 18. Further, the transmitting/receiving circuit 74 subjects the radio wave 14a received by the antenna 18 to amplification and band-pass filtering, and then outputs the radio wave 14a to the demodulator 76.

The DSP 77 subjects the image data demodulated by the demodulator 76 to various kinds of signal processing, and then outputs the image data to a data storage 78. The data storage 78 is, for example, a flash memory having memory capacity of 1 GB, approximately. The data storage 78 stores the image data sequentially outputted from the DSP 77.

A position detector 79 detects a present position of the CE 11 in the human body based on the detection result of the electric field strength of the radio wave 14a detected by the electric field strength detector 19, and outputs the detection result (hereinafter referred to as position information) to the data storage 78 and a data analyzer 81. The data storage 78 stores the position information from the position detector 79 in relation with the image data from the DSP 77.

Note that a specific method for detecting the position of the CE 11 in the human body is as follows. The distribution of electric field strength of the radio wave 14a received by plural antennas 18 based on the position of the CE 11 in the human body are preliminarily obtained in an experiment, and a data table in accordance with a relation between the electric field strength and the position of the CE 11 is preliminarily stored in the ROM 72. Thereafter, the detection result of the electric field strength detector 19 is compared with the distribution of electric field strength in the data table, and thereby the position of the corresponding CE 11 is retrieved from the data table.

Alternatively, deviation amount of time taken for the radio wave 14a to reach the respective antennas 18, namely, phase difference of the radio wave 14a is detected, and then based on the phase difference, the position of the CE 11 is detected. In this case, the phase difference of the radio wave 14a denotes the positional relation (distance) between each antenna 18 and the CE 11. The position detector 79 uses an adequate conversion equation and data table to convert the phase difference of the radio wave 14a to the distance between each antenna 18, and the CE 11, and thereby detects the position of the CE 11. Further, the position of the CE 11 may be detected by detecting arrival directions of radio wave 14a toward at least two antennas 18 and referring to a triangulation principle in which the distance between two antennas 18 is considered as a base length.

The data base 80 stores the diagnostic information from the processor 20. The diagnostic information includes image data of an area around the region diagnosed or doubted as a lesion by a doctor in a past capsule endoscopy for the patient 10 in, for example, a routine medical examination, and position information related to the image data. Moreover, in a case where the patient 10 had surgery and then have the capsule endoscopy for a diagnosis of the surgery region, the diagnostic information further includes the position information that is coordinate data of the surgery region. (In some cases, the doctor operates the user interface 21 to input the position information.)

The data analyzer 81 retrieves the diagnostic information from the data base 80, and compares the position information transmitted from the position detector 79 (hereinafter referred to as present position information) with the position information included in the diagnostic information (hereinafter referred to as past position information). Further, the data analyzer 81 compares the image data transmitted from the CE 11 (hereinafter referred to as present image data) with the image data included in the diagnostic information (hereinafter referred to as past image data). The data analyzer 81 outputs the comparison results to the CPU 70.

The comparison result between the present position information and the past position information serves as a scale to show how close the present position of the CE 11 is to the region diagnosed as a lesion in the past or the surgery region (hereinafter, referred to as target region). Namely, as the extent of conformity of the present position information with the past position information is higher, the present position of the CE 11 is at a periphery of the target region. The data analyzer 81 outputs an evaluation value showing, for example, the extent of conformity between the present position information and the past position information (hereinafter referred to as position evaluation value) as the comparison result.

Also, the comparison result between the present image data and the past image data serves as a scale to show whether or not the region now being shot by the CE 11 is at a periphery of the target region. Namely, as the extent of conformity of the present image data with the past image data is higher, it is considered that the target region and its periphery are being shot. The data analyzer 81 outputs an evaluation value showing, for example, the extent of conformity between the present image data and the past image data (hereinafter referred to as image feature value) as the comparison result.

The data analyzer 81 applies a well-known face detection technology used in a digital camera (see, for example, Japanese Patent Laid-Open Publication No. 2005-284203, Japanese Patent Laid-Open Publication No. 2005-286940, and Japanese Patent Laid-Open Publication No. 2005-156967) to calculate the image feature value. Specifically, for example, the target region in the past image data is used as a template, and the extent of conformity of shape and color between the template and each predetermined region in the present image data (search area) is detected. At this time, while the size and angle of the search area are varied, detection is performed in an entire area in the present image data. The area in which the extent of conformity is highest is judged as the target region, and the size of the area is considered as the image feature value.

In addition to the above components, to the bus 71, there are connected a driver 82 for performing display control of the LCD 15, a communication interface (I/F) 84 serving for exchange of data with the processor 20 via a USB connector 83, a power source 86 for supplying the electric power of a battery 85 to each component of the receiver 12, and the like.

The CPU 70 produces the control command in accordance with the position evaluation value and the image feature value. The CPU 70 outputs the produced control command to the modulator 75. The control command is for controlling the frame rate of image sensor 33, and can set three stages of frame rate, that is, 16 fps (frame/second), 4 fps, and 1 fps.

Now, the transitional changes in the position evaluation value and the image feature value are considered. At first, in the region away from the target region, the position evaluation value and image feature value are low. As the distance toward the target region is shorter, the position evaluation value and the image feature value become higher. At a periphery of the target region, the present position information and the past position information as well as the present image data and the past image data approximately correspond to each other. Moreover, the position evaluation value and the image feature value become highest. As the CE 11 moves away from the target region, the position evaluation value and the image feature value gradually become lower, and until the CE 11 approaches the target region next time, the position evaluation value and the image feature value remain as low as the initial value.

In view of the above consideration, for the purpose of decreasing the number of images unnecessary for diagnosis and obtaining the images of the target region and its periphery to be focused in the diagnosis as much as possible, it is only necessary to lower the frame rate when the CE 11 is away from the target region, and raise the frame rate when the CE 11 is at the periphery of the target region.

That is to say, when the CE 11 is away from the target region and further both the position evaluation value and the image feature value are low, the CPU 70 produces the control command with the frame rate set at 1 fps. Additionally, when the CE 11 is near the target region and further the position evaluation value becomes equal to or more than a first threshold value, the CPU 70 produces the control command with the frame rate set at 4 fps.

Moreover, when the CE 11 is in the target region or the periphery thereof and further the image feature value is equal to or more than a second threshold value, the CPU 70 produces the control command with the frame rate set at 16 fps. Note that, at this time, although the position evaluation value is also equal to or more than the first threshold value, regardless of the position evaluation value, when the image feature value is equal to or more than a second threshold value, the frame rate is set at not 4 fps but 16 fps. Therefore, the first threshold value is set such that the position of the CE 11 when the position evaluation value exceeds the first threshold value is before the position of the CE 11 when the image feature value exceeds the second threshold value with respect to the target region. Therefore, the frame rate surely shifts from 1 to 4, and then from 4 to 16. The frame rate does not shift from 1 to 16.

Moreover, when the CE 11 passes through the target region and both position evaluation value and image feature value become less than the first threshold value and the second threshold value, respectively, the CPU 70 produces the control command with the frame rate set at 4 fps. After the CE 11 moves away from the target region, and further both the position evaluation value and the image feature value become as low as the initial values, at the time when a predetermined time has elapsed with keeping this state, the CPU 70 produces the control command with the frame rate set at 1 fps. Namely, in accordance with the movement of the CE 11, the frame rate set by the control command changes. Concretely, when the CE 11 is away from the target region, the frame rate is set at 1 fps. When the CE 11 is near the target region, the frame rate is set at 4 fps. When the CE 11 at the periphery of the target region, the frame rate is set at 16 fps. When the CE 11 has passed through the target region, the frame rate is set at 4 fps. When the CE 11 becomes away from the target region, the frame rate is at 1 fps. Note that the last frame rate, and the time which has elapsed since the frame rate was set at 4 fps are stored as the data in the RAM 73. Here, "near the target region" is defined as a region between the "region away from the target region" and "the periphery of target region", and bit more away from the target region than "the periphery of the target region".

Figure 5:
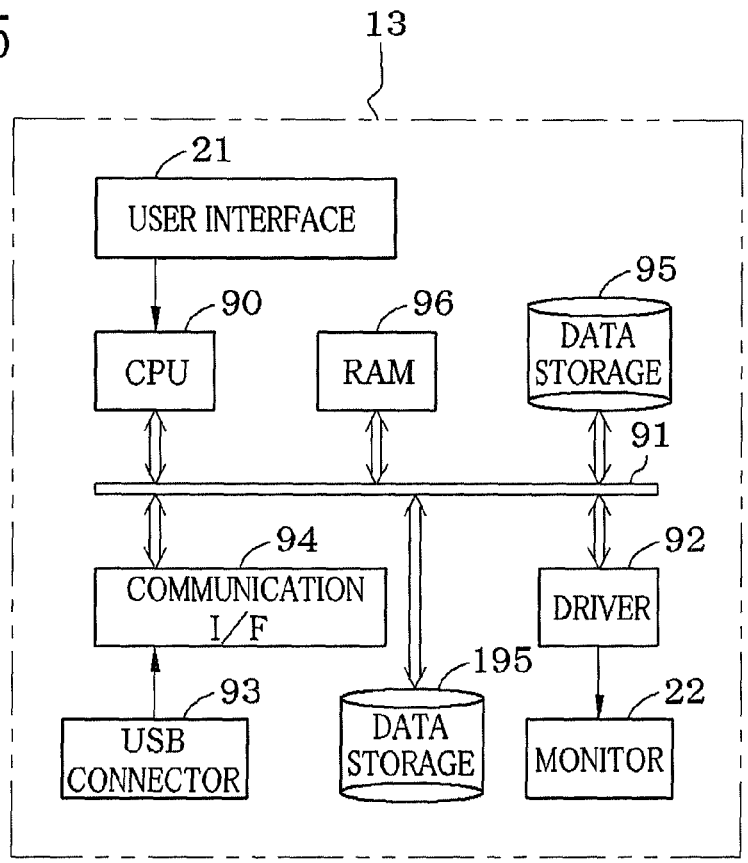
FIG. 5 is a block diagram illustrating an electrical configuration of a work station.

As shown in FIG. 5, a CPU 90 controls all the operation of the WS 13 as a whole. A driver 92 for performing display control of the monitor 22, a communication I/F 94 serving for exchange of data with the receiver 12 via a USB connector 93 and receiving the image data from the receiver 12, a data storage 95, and a RAM 96 are connected to the CPU 90 via a bus 91.

The data storage 95 stores diagnostic information arranged for each patient together with various programs and data necessary for the operation of the WS 13 and a program of support software for supporting the doctor in the diagnosis. The RAM 96 temporarily stores the data retrieved from the data storage 95, and intermediate data generated in various kinds of arithmetic processing. When the support soft is launched, the operation window of the support soft is displayed on the monitor 22, for example. The doctor can display and edit the image and input the diagnostic information by operating the user interface 21 on the operation window described above.

Figure 7:
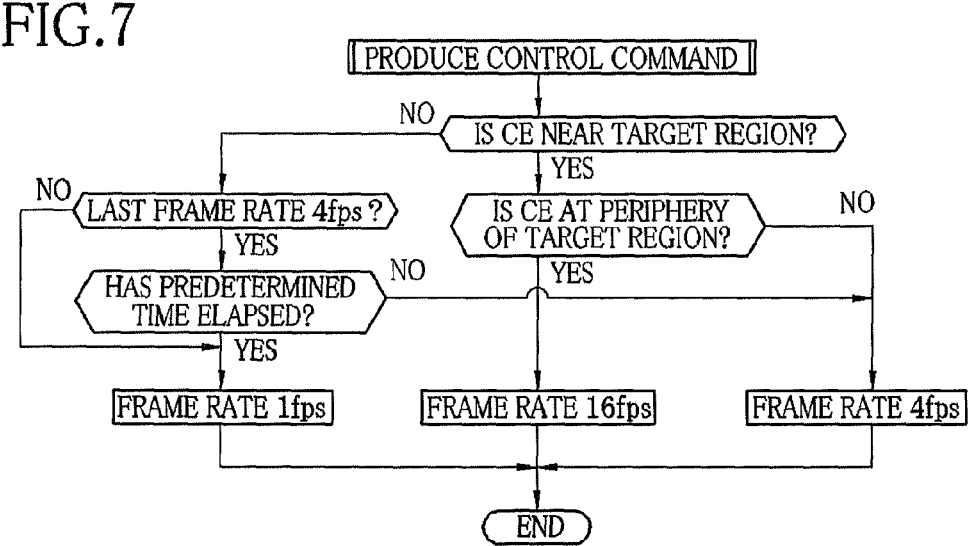
FIG. 7 is a flowchart illustrating a procedure of producing a control command.
Figure 6:
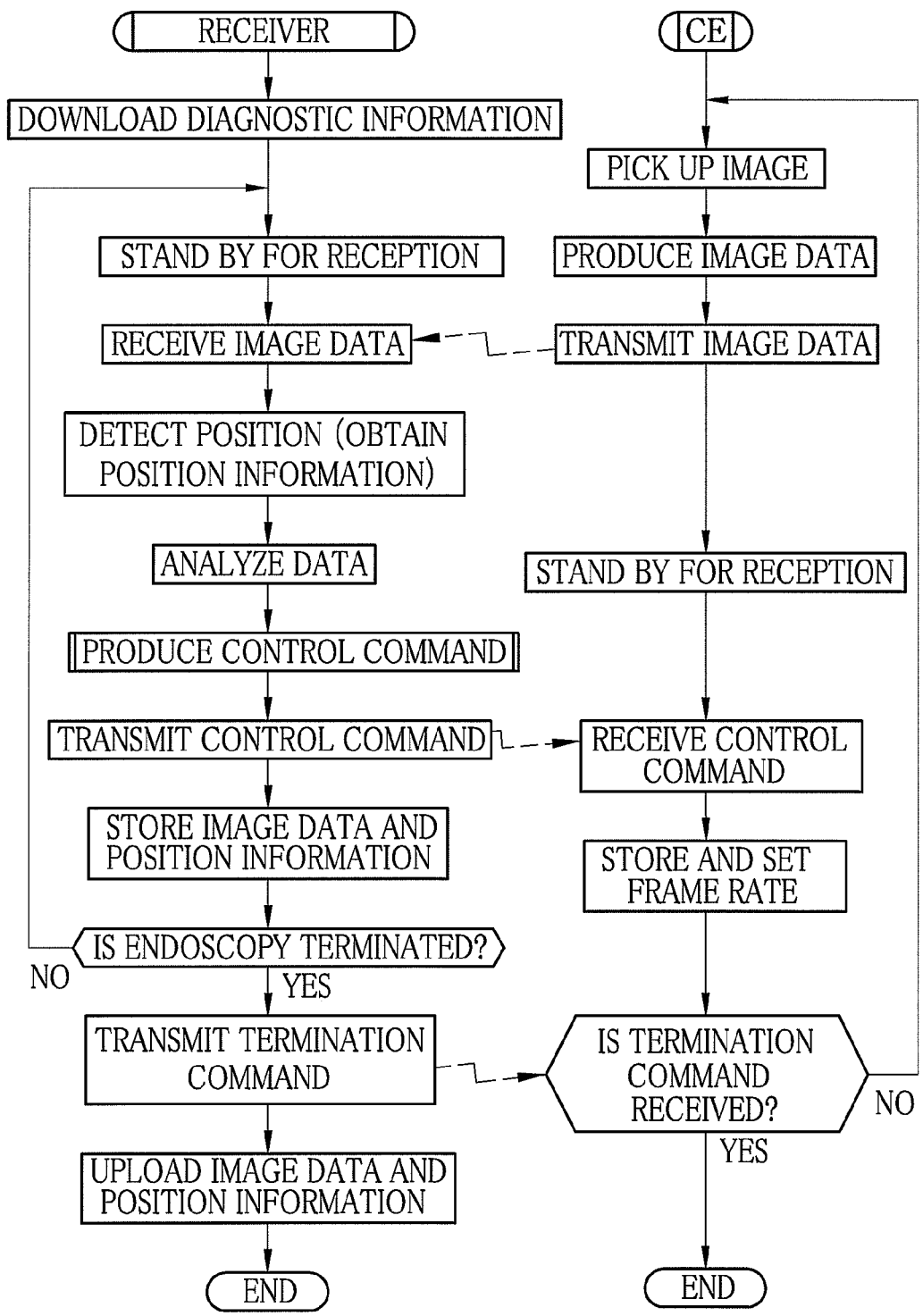
FIG. 6 is a flowchart illustrating a procedure of capsule endoscopy.
Figure 8:
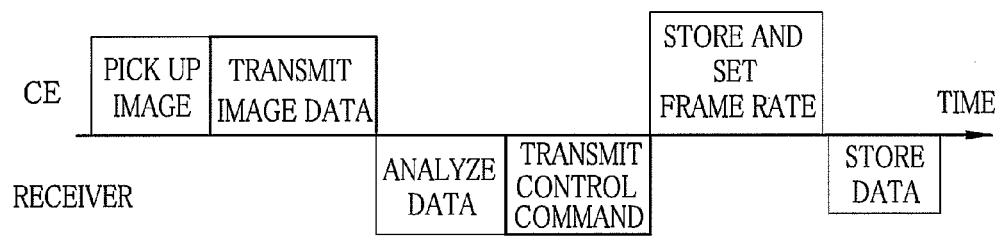
FIG. 8 is a timing chart illustrating the procedure of the capsule endoscopy.

Next, the procedure of endoscopy by the capsule endoscopic system configured as described above is described by referring to the flowcharts in FIGS. 6 and 7, and the timing chart in FIG. 8. First of all, as preparation before the endoscopy, the doctor connects the receiver 12 to the processor 20 through the USB cable 23, and downloads the diagnostic information of the patient 10 to be inspected from the data storage 95 of the WS 13 to the data base 80 of the receiver 12. Secondly, the receiver 12, the shield shirt 17, and the antenna 18 are worn by the patient 10. After being powered on, the CE 11 is taken into a body through a mouth of the patient 10.

When the CE 11 is swallowed by the patient 10 to complete the preparation of the endoscopy, the inner wall surface of the tracts in the human body is shot by the image sensor 33 at the frame rate of the initial setting, namely, 1 fps, while the region to be observed in the human body is illuminated by the light source section 36. At this time, the image light in the region to be observed in the human body, which has entered through the objective optical system 32, is focused on the pickup surface of the image sensor 33, and thereby the pickup signal is outputted from the image sensor 33. The pickup signal outputted from the image sensor 33 is subjected to related double sampling, amplification, and A/D conversion by the signal processor 54, and then converted into the digital image data and subjected to various kinds of image processing.

The digital image data outputted from the signal processor 54 is modulated to the radio wave 14*a* by the modulator 56. The modulated radio wave 14*a* is subjected to amplification and band-pass filtering by the transmitting/receiving circuit 55, and transmitted from the antenna 39.

Being received by the antenna 18 of the receiver 12, the radio wave 14*a* is subjected to amplification and band-pass filtering by the transmitting/receiving circuit 74, and then demodulated into the original image data by the demodulator 76. The demodulated image data is subjected to various kinds of signal processing by the DSP 77 and then outputted to the data storage 78.

Moreover, at this time, the electric field strength of the radio wave 14*a* is detected by the electric field strength detector 19. Thereafter, based on the detection result of the electric field strength detector 19, the position of the CE 11 in the human body is detected by the position detector 79. The detection result of the position detector 79, that is, the position information is outputted to the data storage 78 and the data analyzer 81.

The diagnostic information is retrieved from the data base 80 in the data analyzer 81. Then, the present position information and the past position information as well as the present image data and the past image data are compared with each other, and the position evaluation value and the image feature value are outputted as the comparison results. The position evaluation value and the image feature value are inputted to the CPU 70.

Upon receiving the position evaluation value and the image feature value from the data analyzer 81, the CPU 70 produces the control command by the procedure shown in FIG. 7. That is to say, when the position evaluation value is equal to or less than the first threshold value (when "IS CE NEAR TARGET REGION?" is "NO") and the frame rate set last time is not 4 fps (when the CE 11 is away from the target region, and the position evaluation value and the image feature value are low), the frame rate is set at 1 fps. When the position evaluation value is equal to or more than the first threshold value (when "IS CE NEAR TARGET REGION?" is "YES") and when the image feature value is equal to or less than the second threshold value (when "IS CE AT PERIPHERY OF TARGET REGION?" is "NO") (when the CE 11 is near the target region), the frame rate is set at 4 fps. When the image feature value is equal to or more than the second threshold value (when "IS CE AT PERIPHERY OF TARGET REGION?" is "YES") and the position evaluation value is equal to or more than the first threshold value (when the CE 11 is at a periphery of the target region), the frame rate is set at 16 fps.

In a case where the position evaluation value is equal to or less than the first threshold value and the image feature value is equal to or less than the second threshold value, when the frame rate set last time is 4 fps, and a predetermined time has not elapsed since the frame rate was set at 4 fps (when the CE 11 passes through the target region), the frame rate is maintained at 4 fps. In a case where the position evaluation value is equal to or less than the first threshold value, the image feature value is equal to or less than the second threshold value, when the frame rate set last time is 4 fps, and a predetermined time has elapsed since the frame rate was set at 4 fps (when the CE 11 moves away from the target region), the frame rate is set at 1 fps.

Returning to FIG. 6, the control command with the frame rate set as described above by the CPU 70 is modulated into the radio wave 14*b* by the modulator 75. The modulated radio wave 14*b* is subjected to amplification and band-pass filtering by the transmitting/receiving circuit 74, and then transmitted from the antenna 18. After the control command is transmitted via the radio wave 14*b*, the image data transmitted from the DSP 77 and the position information from the position detector 79 are related to each other and stored in the data storage 78 in the receiver 12.

Being received by the antenna 39 of the CE 11, the received radio wave 14*b* is outputted to the demodulator 57 by the transmitting/receiving circuit 55 in the CE 11. The radio wave 14*b* outputted to the demodulator 57 is demodulated to the original control command by the demodulator 57, and then outputted to the CPU 50. The data of the frame rate specified by the control command is temporarily stored in the RAM 52.

The data of the frame rate stored in the RAM 52 is retrieved to the driver 53. The operation of the image sensor 33 and the signal processor 54 are controlled by the driver 53 such that image shooting is preformed at the frame rate specified by the control command, that is, one of 1, 4, and 16 fps. A series of processes described above are repeated until the endoscopy is terminated and the termination command is transmitted from the receiver 12 to the CE 11 via the radio wave 14b.

After the endoscopy, the doctor connects the receiver 12 to the processor 20 through the USB cable 23 again, and uploads the image data stored in the data storage 78 and the position information related with the image data to the data storage 95 of the WS 13. Thereafter, diagnosis is conducted by use of the support software in the WS 13.

As shown in the timing chart of FIG. 8 illustrating the process at the time of starting the endoscopy, at first, the image shooting is performed at the frame rate of 1 fps (at the initial setting) by the CE 11, and then the image data thus obtained is transmitted via the radio wave 14a to the receiver 12. Upon receiving the radio wave 14a, the data is analyzed in the receiver 12 to produce the control command, and then the produced control command is transmitted via the radio wave 14b to the CE 11.

Upon receiving the radio wave 14b, the frame rate specified by the control command is stored and set in the CE 11. The frame rate set at this time is reflected in the next image shooting. On the contrary, the receiver 12 stores the image data and the position information. Namely, in this embodiment, the region to be observed is shot by the CE 11 at first, and then the image data is transmitted/received between the CE 11 and the receiver 12. Thereafter, the control command is produced and transmitted/received, and the frame rate is stored and set (corresponding to a first operation mode).

Figure 9A:
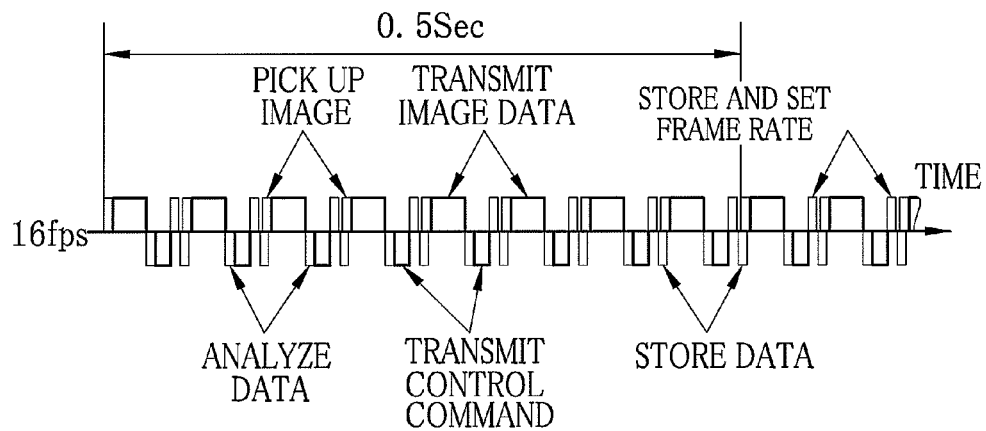
FIGS. 9A to 9C are timing charts illustrating the procedure of the capsule endoscopy in which FIG. 9A at a frame rate of 16 fps, FIG. 9B at a frame rate of 4 fps, and FIG. 9C at a frame rate changed from 16 fps to 4 fps.

In a case where the frame rate is set at 16 fps, the process in the CE 11 and the receiver 12 is as shown in FIG. 9A. That is to say, one process sequence shown in FIG. 8 (CE 11: image shooting, transmission of the image data, and storing and setting of the frame rate are performed in this order; and receiver 12: analysis of data, transmission of the control command, and storing of the data are performed in this order) is repeated 16 times at regular intervals in one second (8 times in 0.5 second).

Figure 9B:
Figure 9C:
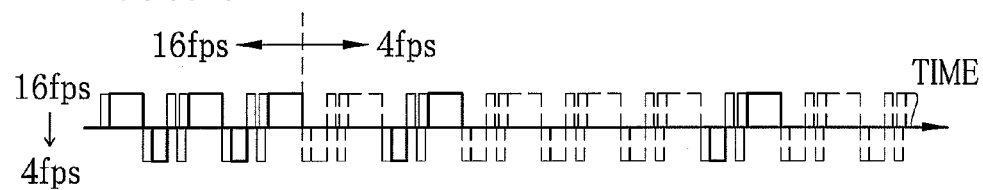

Further, in a case where the frame rate is set at 4 fps, as shown in FIG. 9B, after one process sequence is conducted, the next three process sequences are omitted. Therefore, the process sequence is conducted 4 times at regular intervals in one second (twice in 0.5 second). Similarly, in a case where the frame rate is set at 1 fps, after one process sequence is conducted, the next 15 process sequences are omitted, and one process sequence is conducted in one second. Further, as shown in FIG. 9C, in a case where the setting of the frame rate is changed from 16 fps to 4 fps, one process sequence is omitted at the time of changing from 16 fps to 4 fps.

As described above, based on the comparison result between the present information obtained during the endoscopy and the past diagnostic information, the frame rate for image shooting by the CE 11 is set, and therefore it is possible to obtain a large amount of images of a target region, which is desired to be read in detail during diagnosis. Accordingly, there is no fear that the image of the target region is not be shot. Moreover, in a case where a routine medical examination for wait-and-see approach of the target region or a post-surgery inspection is performed, it is possible to conduct diagnosis correctly and rapidly.

Additionally, since the amount of the images of region other than the target region, unnecessary for the diagnosis, decreases, the amount of images to be read in the diagnosis becomes less in comparison with the case where image shooting is performed at a fixed frame rate, and burden on the doctor can be decreased. Further, since the amount of images decreases, the capacity of the data storage 78 can be small, and therefore it is possible to reduce the cost of components. Furthermore, since the number of shooting images becomes less in comparison with the case where image shooting is performed at a fixed frame rate, it is possible to suppress electricity consumption for image shooting and transmission of the image data, and therefore it is also possible to prolong the lifetime of the CE 11. Note that, although the amount of images of the target region is increased, the target region occupies small area of the human body. Therefore, it can be easily comprehended that if the amount of the images of region other than the target region, which occupies large area of the human body, decreases, the total amount of images and number of shooting images decrease in comparison with a case where image shooting is performed at a fixed frame rate.

In the above embodiment, although image shooting by the CE 11 is performed at the frame rate specified by the control command, alternatively or additionally, the control command may be a release signal for one image shooting by the CE 11, and then the CE 11 may shoot an image of the region to be observed once in accordance with the reception of the control command (corresponding to a second operation mode). In this case, as shown in the flow chart of FIG. 10 and the timing chart of FIG. 11, the process for the endoscopy is slightly different from that in the above embodiment.

Figure 10:
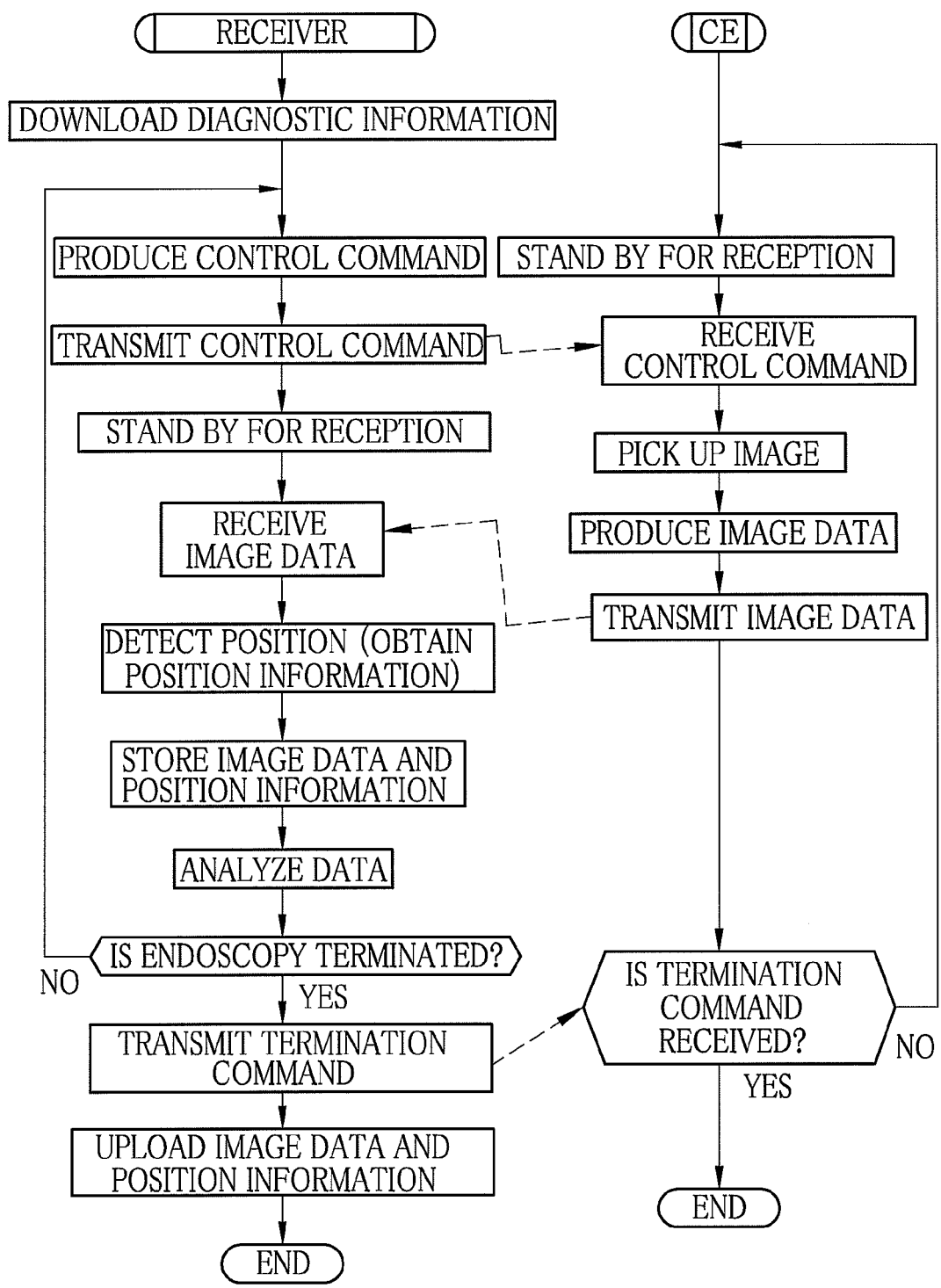
FIG. 10 is a flowchart illustrating a procedure of capsule endoscopy when the control command is the release signal.
Figure 11:
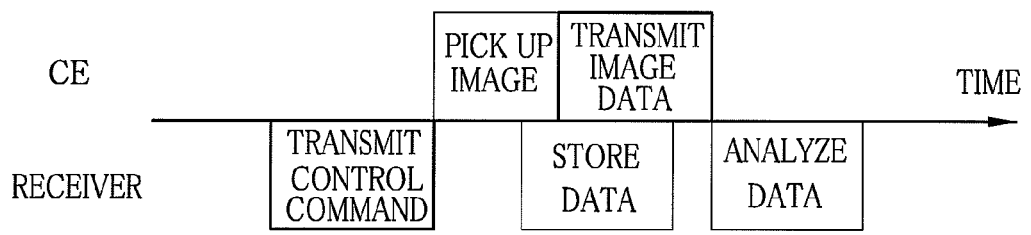
FIG. 11 is a timing chart illustrating the procedure of capsule endoscopy when the control command is the release signal.

In FIGS. 10 and 11, when the diagnostic information is downloaded and the preparation for the endoscopy is completed, the control command is transmitted from the receiver 12 to the CE 11 via the radio wave 14b.

Upon receiving the radio wave 14b by the antenna 39, unlike the above embodiment, the CE 11 does not store and set the frame rate, but immediately shoots an image once, and the obtained image data is transmitted to the receiver 12 via the radio wave 14a.

In the receiver 12, after the position is detected and the position information thus obtained and the image data are stored in relation with each other, the data is analyzed as in the case of the above embodiment. In a case where the CE 11 is away from the target region, the control command is produced at an adequate interval and transmitted via the radio wave 14b. When the CE 11 is near the target region, or when the CE is at a periphery of the target region, the control command is produced at an interval shorter than when the CE 11 is away from the target region, and transmitted via the radio wave 14b. In the CE 11, each time the radio wave 14b is received, image shooting is performed once. The series of processes described above are repeated until the termination command is transmitted as in the case of the above embodiment.

Figure 12:
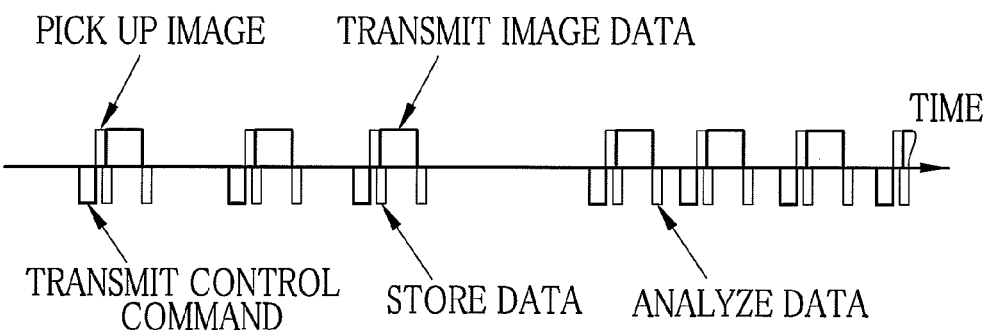
FIG. 12 is a timing chart illustrating the procedure of capsule endoscopy when the control command is the release signal.

As described above, the control command is the release signal, and at the timing of receiving the control command, image shooting is performed. Therefore, unlike the above embodiment in which image shooting is performed at a predetermined interval, it is possible to perform image shooting at an arbitrary interval as shown in FIG. 12.

Note that if the first operation mode in which image shooting is performed at the frame rate specified by the control command and the second operation mode in which image shooting is performed once upon receiving the control command are used in combination, the control command may be used for changeover between the first and second operation modes.

In a case where it is unnecessary to perform shooting so frequently such as when the CE 11 is away from the target region and a predetermined time has elapsed or when it takes some time for the CE 11 to reach the next target region, it is possible to halt the operation of the components related to image shooting such as the image sensor 33, the driver 53, and the signal processor 54 (corresponding to a third operation mode). Also in this case, the changeover to the third operation mode is performed by the control command. Further, in this case, since no image shooting is performed, the image data is not transmitted via the radio wave 14*a* as a matter of course. However, the radio wave 14*a* is transmitted periodically as a beacon signal for position detection. Note that if there is no need for position detection, it is possible to halt the operation of the transmitting/receiving circuit 55 and modulator 56, and the beacon signal may not be transmitted.

Note that an operation condition for the light source section may be set by the control command. In this case, a light source section 101 in a CE 100 as shown in FIG. 13 is configured, for example.

Figure 13:
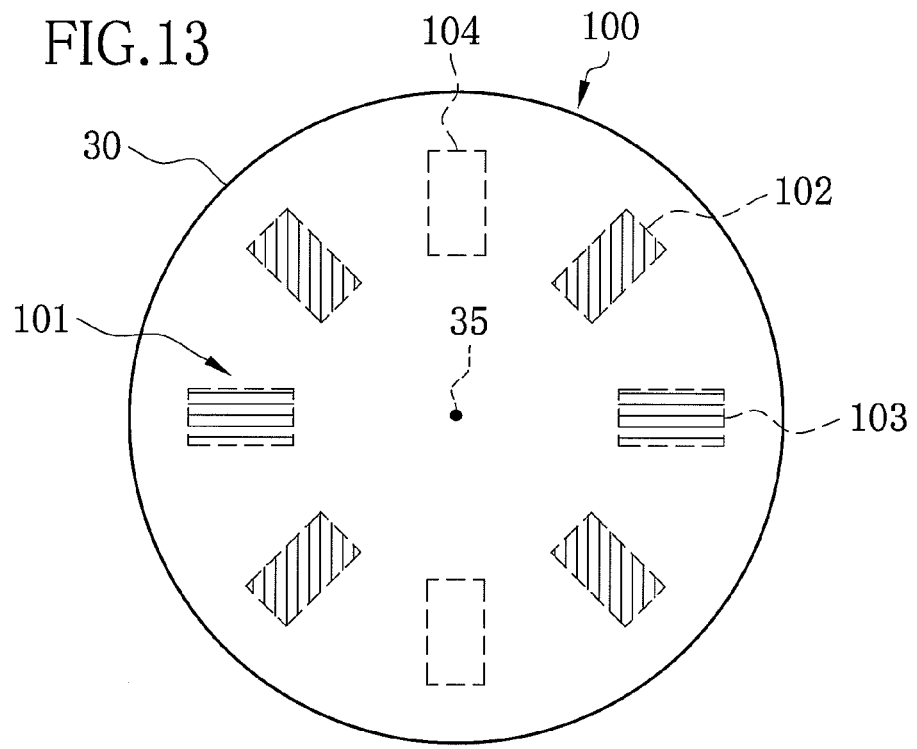
FIG. 13 is a plan view illustrating a light source section according to another embodiment of the present invention.

As shown in FIG. 13, in which the CE 100 is viewed in front of the front cover 30, the light source section 101 includes four short-range light sources 102 (shown by vertical hatching lines), two long-range light sources 103 (shown by horizontal hatching lines), and two non-white light sources 104, namely in total eight light sources. The short-range light sources 102 are concentrically deposited around the optical axis 35 at the same interval by making an angle of 90°. Each of the long-range light sources 103 is deposited so as to be deviated from the short-range light source 102 by making an angle of 45° and sandwiched between the adjacent short-range light sources 102. Similarly, each of the non-white light sources 104 is deposited so as to be deviated from the short-range light source 102 by making an angle of 45° and sandwiched between the adjacent short-range light sources 102.

Figure 14:
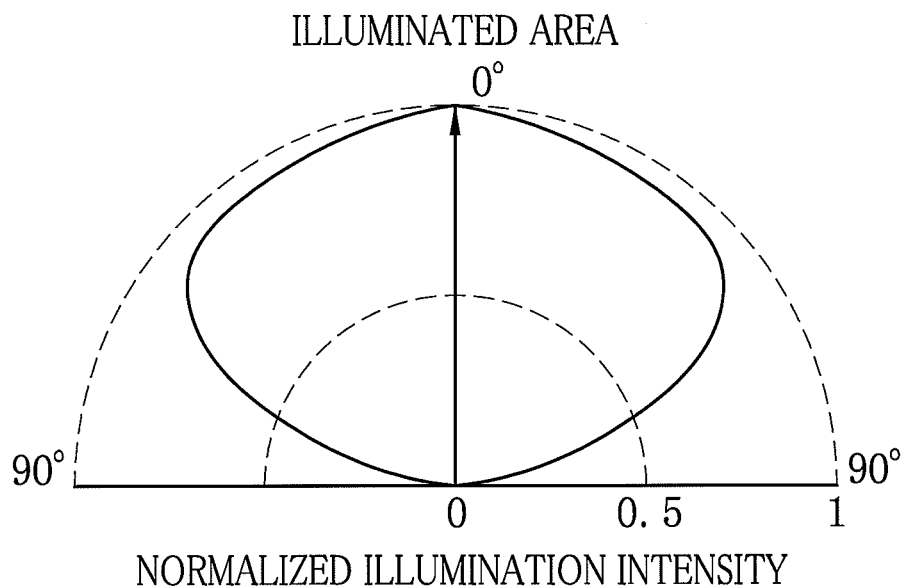
FIG. 14 is an explanatory view illustrating a directional pattern of a short-range light source.
Figure 15:
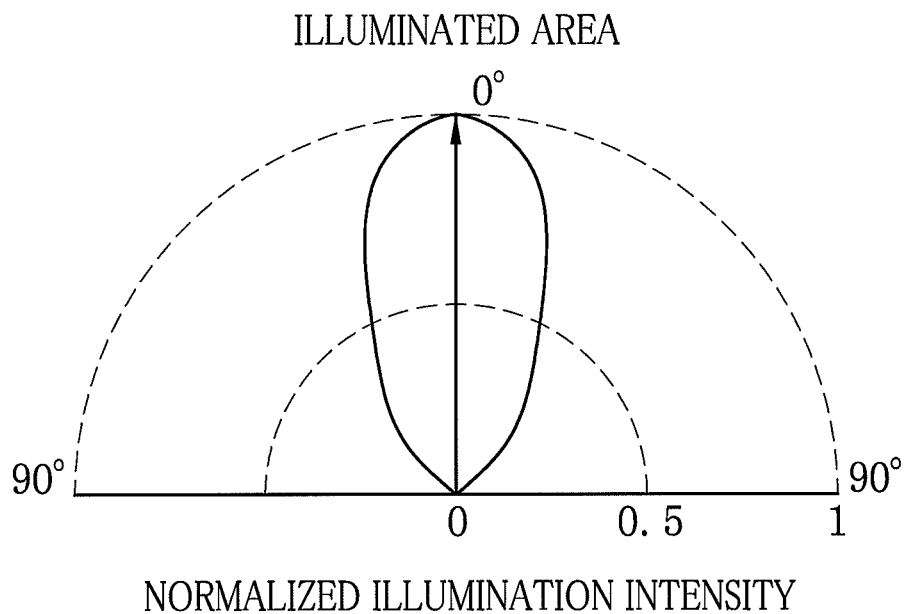
FIG. 15 is an explanatory view illustrating a directional pattern of a long-range light source.

As shown in FIG. 14, the short-range light source 102 is a white light source having a directional pattern in which a certain degree of illumination intensity can be achieved at a relatively wide illumination range. The illumination distance of the short-range light source 102 is relatively short. Further, as shown in FIG. 15, the long-range light source 103 is a white light source having a directional pattern in which a sufficient degree of illumination intensity can be achieved at an illumination range narrower than that of the short-range light source 102. The long-range light source 103 has an illumination distance longer than that of the short-range light source 102. The non-white light source 104 is a light source emitting light whose wavelength band is different from that of the white light source, such as red, blue, and green light, for the purpose of obtaining a spectrum image.

In this case, in accordance with the positional relation between the CE 100 and the target region, the light sources to be lightened are changed. For example, when the CE 100 is away from the target region, for the purpose of facilitating discovery of the target region, two short-range light sources 102 opposed to each other and all the long-range light sources 103 are lightened. When the CE 100 is near the target region, all the short-range light sources 102 and all the long-range light sources 103 are lightened. When the CE 100 is at a periphery of the target region, for the purpose of obtaining clear images of the target region, all the short-range light sources 102 are lightened, and the long-range light sources 103 are turned off. Alternatively, electricity supplied to the short-range light sources 102 and the long-range light sources 103 or lightening time of the light sources may be controlled in order to provide an appropriate light amount corresponding to the positional relation between the CE 100 and the target region. Thereby, it is possible to perform image shooting under the optimum lighting environment all the time, and obtain clear images of the target region to be used for accurate diagnosis. Further, it is also possible to suppress the consumption of electricity necessary for the operation of the light source section to the minimum extent.

Although the electric field strength detector 19 is used to obtain the position information in the above embodiment, alternatively, it is also possible to dispose a magnet on the CE 11 and a hall element on the antenna 18 to measure the strength of magnetic field of the magnet, and then detect the position of the CE 11 in the human body by use of the position detector 79 based on the measurement result of the hall element. Further, instead of the electric field strength detector 19, the hall element, and the like, it is also possible to provide the receiver 12 with, for example, an image analyzer for analyzing the image data by use of a well-known image analysis technology and analyze the image data from the CE 11 by the image analyzer in order to detect the position of the CE 11. In this case, for example, a typical image of particular region in an internal organ is prepared as a template, and based on the degree of conformity between the template and the image data transmitted from the CE 11, the position of the CE 11 is detected.

Alternatively, it is possible to detect the position of the CE 11 not directly but indirectly. For example, the operation time of the CE 11 which has elapsed since the CE 11 was taken into a body and the endoscopy started is measured, and instead of or in addition to the position of the CE 11 detected directly in the above embodiment, based on the measurement result, the control command may be produced. In this case, the operation time is measured by, for example, a built-in clock 50*a* in the CPU 50 or a built-in clock 70*a* in the CPU 70 (see FIGS. 3 and 4, respectively) Alternatively, in a case where image shooting was performed at a fixed frame rate in the first endoscopy, the operation time is measured by the number of the accumulated image data. Then, as in the case of the position in the above embodiment, the operation time is stored in relation with the image data. In subsequent endoscopy, an evaluation value representing the degree of conformity between the measured present operation time and the stored past operation time measured, and based on the measured evaluation value, the control command is produced.

Figure 16:
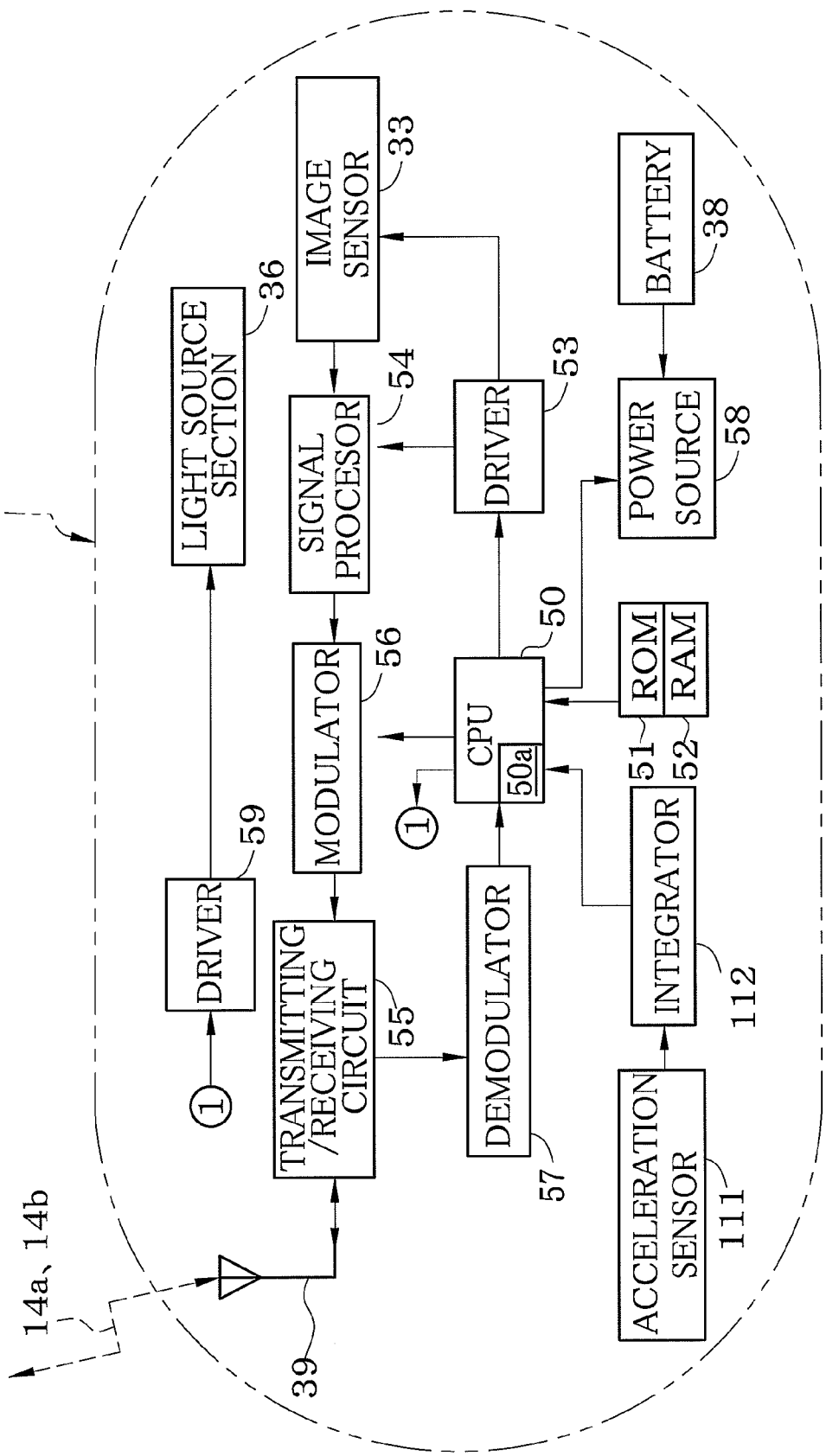
FIG. 16 is a block diagram illustrating an electrical configuration of a capsule endoscope provided with an acceleration sensor and an integrator.

Moreover, for example, the moving distance of the CE since the CE was taken into the body and endoscopy started is measured, and instead of or in addition to the position and the operation time, based on the measurement result, the control command may be produced. In this case, such as a CE 110 shown in FIG. 16, an acceleration sensor 111 and an integrator 112 are disposed.

The acceleration sensor 111 is a three-axis acceleration sensor capable of measuring acceleration of three axes, for example, X, Y, and Z. The acceleration sensor 111 measures acceleration of two axes, one of which is in the advancing direction of the CE 110 (a direction parallel to the optical axis 35 extending from the side of the rear cover 31 to the side of the front cover 30) and the other of which is in a direction perpendicular to the advancing direction, and outputs the measurement result to an integrator 112. The integrator 112 integrates the measurement result of the acceleration sensor 111 twice at a certain interval to obtain the moving distance of the CE 110, and outputs the data of the moving distance to the CPU 50.

The CPU 50 integrates the moving distance sequentially outputted from the integrator 112 and calculates the total moving distance of the CE 110. Further, as in the case of the position and the operation time, the moving distance is stored in relation with the image data. In the endoscopy, as in the case of the position and the operation time, the control command is produced. As described above, if not only the position of the CE detected directly, but also operation time and the moving direction are used together as the position information, more accurate positional relation between the CE and the target region can be detected.

Figure 17:
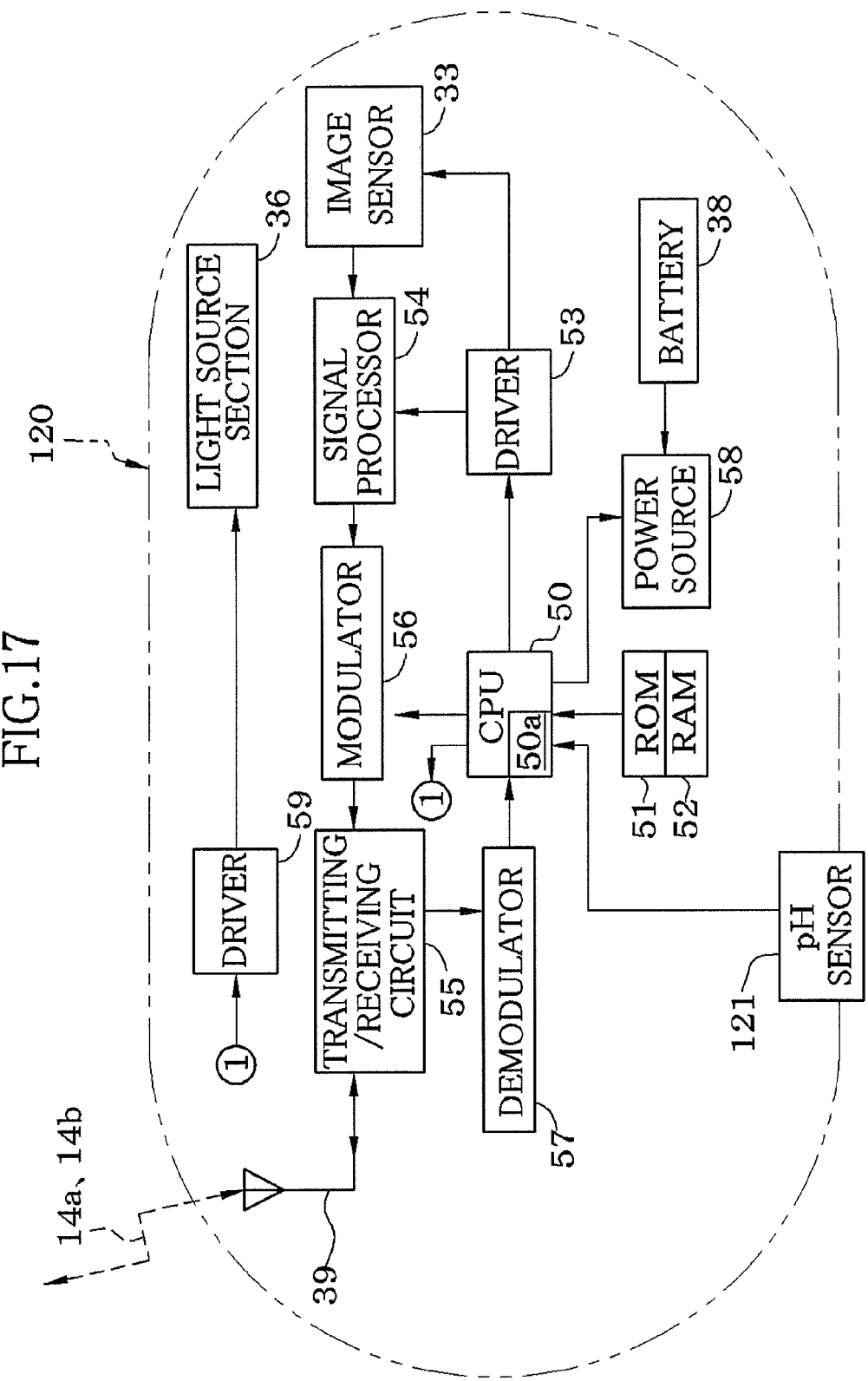
FIG. 17 is a block diagram illustrating an electrical configuration of a capsule endoscope provided with a pH sensor.

Moreover, instead of the operation time and moving distance since the endoscopy started, it is possible to detect the passage of the CE through a pylorus which is an exit of stomach, and consider the timing of detection as a reference point (zero point) of the operation time and the moving distance. In this case, for example, such as a CE 120 shown in FIG. 17, a pH sensor 121 is incorporated in the CE.

A sensor section of the pH sensor 121 is exposed through the both covers 30 and 31. The pH sensor 121 measures the pH of the tracts in the human body and outputs the measurement result to the CPU 50. At the time when the CE 120 passes through the pylorus, the stomach is strongly acidic (pH of 1 to 3), and the small intestine connected to the stomach is alkaline, and therefore the measurement result of the pH sensor 121 changes from acidic to alkaline. The change in the measurement result of the pH sensor 121 is monitored by the CPU 50, and at the time when the measurement result changes from acidic to alkaline, the CPU 50 causes the pH sensor 121 to transmit the signal representing the state via the radio wave 14a.

When the signal representing that the measurement result of the pH sensor 121 changes from acidic to alkaline is received via the radio wave 14a, the receiver 12 starts measuring the operation time or the moving distance of the CE (in this case, the acceleration sensor 111 and the integrator 112 are disposed in the CE 120). Thereby, the time taken for the CE to pass through the stomach and the moving distance of the CE, which are varied depending on the patients, can be canceled. Further, accurate position information of the internal organs after the small intestine, which is to be focused especially in the capsule endoscopy, can be obtained. Note that instead of the pH sensor 121, a well-known image recognition technology may be used to analyze the image data by the receiver 12, and based on the analysis result, the passage of the CE through the pylorus may be detected. Note that in this case image recognition with high resolution is not necessary, and it is sufficient to recognize the stomach and regions other than the stomach.

The method for detecting the position information described heretofore is an example, and the present invention is not limited thereto. In conclusion, it is only necessary to identify the position of the CE in the human body. Any method other than those describe above may be used.

Although the control command is produced based on the diagnostic information in the above embodiment, in this case, the application is limited to only the patient who has been subjected to the capsule endoscopy before or has had surgery. In view of the above, in addition to the diagnostic information, based on case information obtained from a typical instance of disease, the control command may be produced. The case information is stored in the WS 13 in storage section 195 and in the receiver 12 in database 180. The case information includes image data of lesion and its vicinity obtained by the capsule endoscopy of other patients, lesion having typical characteristic amount such as shape, color, and size, or image data of foreign materials such as worms and food debris. Namely, the case information is obtained by selecting typical data among large amount of data accumulated by past diagnosis.

In this case, as in the case of the above embodiment, the present image data and the image data of case information are compared with each other to calculate the image feature value by data analyzer 181. Thereby, the control command is produced in accordance with the image feature value in the CPU 70. However, in this case, since the case information includes no position information, the calculation of position evaluation value and production of the control command based on the position evaluation value are not performed.

Accordingly, it is possible to perform the same process as in the case where the control command is produced based on the diagnostic information. Therefore, it is possible to deal with a first-time patient for the capsule endoscopy. Further, it is possible to find lesion which did not appear in the last endoscopy, and therefore lesion other than the region whose postoperative course is to be observed (incidental lesion) can be found. Note that the case information may be stored in the database 80 of the receiver 12 and in the data storage 95 of the WS 13 each of which is used for storing the diagnostic information. Additionally, it is also possible to dispose a data base and a data storage dedicated for the case information. Similarly, the data analysis may be performed in the data analyzer 81 used for the diagnostic information or a dedicated data analyzer.

FIG. 18 shows an example of transition of frame rate embodying each of the above embodiments. Further, an example of the control command is shown in FIG. 19.

In FIG. 18, first of all, when the endoscopy starts, as indicated by "A", the CE is activated at the frame rate of the initial setting, that is, 1 fps. When the CE moves along the tracts in the human body and approaches near the target region, as indicated by "B", the frame rate is changed to 4 fps in order to find the target region. When the CE reaches at a periphery of the target region, as indicated by "C", the setting of the frame rate is changed to 16 fps in order to shoot sufficient number of images. When the CE passes through the target region, as indicated by "D", the frame rate is returned to 4 fps again, in order to find the next target region. When a predetermined time has elapsed since the frame rate was set at 4 fps, as indicated by "E", the frame rate is changed to 2 fps, in order to suppress consumption of electricity.

When a lesion is found in the data analysis based on the case information, as indicated by "F", the frame rate is changed to 16 fps as in the case of "C". When the CE passes through the target region, as indicated by "G", the frame rate is returned to 4 fps again as in the case of "D". When a predetermined time has elapsed since the frame rate was set at 4 fps, as indicated by "H", the frame rate is changed to 2 fps as in the case of "E".

As indicated by "I", when a predetermined time further has elapsed since the frame rate was set at 2 fps, in order to suppress consumption of electricity to the minimum extent, as indicated by "J", the changeover to the third operation mode (low power mode) is performed. In the third operation mode, the image shooting is halted and only the beacon signal for position detection is transmitted.

When a foreign material is found in the data analysis based on the case information, as indicated by "K", the frame rate is changed to 8 fps in order to shoot sufficient number of images. When the CE passes through the foreign material, as indicated by "L", the frame rate is returned to 4 fps again as in the cases "D" and "G".

As shown in FIG. 19, the control command is sorted into a power source system in relation to power control of the CE, an imaging system in relation to operation control of the image sensor 33 and the signal processor 54, an light system in relation to operation control of the light source section 101, a preset for preliminarily setting various operation conditions, and others.

The control command of the power source system includes "Reset" (command 00), "Deep Sleep" (command 02), "Sleep" (command 03), and "Wake-Up" (command 01). "Reset" is issued to reset the system of the CE when the CE is activated or when unexpected failure occurs. "Deep Sleep" is issued to perform changeover to the low power mode in which no beacon signals are transmitted. "Sleep" is issued to perform changeover to the low power mode in which the beacon signals are transmitted. "Wake-Up" is issued to changeover from "Deep Sleep" or "Sleep" to the normal state.

The control command of the imaging system includes "Mode" (command 10(n), index n of 1 corresponding to the first operation mode, index n of 2 corresponding to the second operation mode), "Frame Rate" for setting the frame rate (command 11(n), index n of 1 to 32, frame rate of n/2 fps), and "Release" (command 15). "Mode" is issued to perform changeover between the first operation mode in which image shooting is performed by the CE at a fixed frame rate (consecutive imaging) and the second operation mode in which image shooting is performed by the CE at arbitrary timing (one-shot imaging). "Release" is issued to transmit the control command as the release signal in one-shot imaging.

The control command of the light system includes "KIND OF LIGHT" (command 20(n), index n of 1 to 4, index n of 1 corresponding to the short-range light source 102, index n of 2 corresponding to the long-range light source 103, index n of 3 corresponding to both short-range light source 102 and long-range light source 103, index n of 4 corresponding to non-white light source 104), "NUMBER OF LIGHT SOURCES TO BE LIGHTENED" (command 21(n), index n of 2 and 4, index n of 2 corresponding to the number of light sources to be lightened of 2, index n of 4 corresponding to the number of light sources to be lightened of 4), "LIGHT AMOUNT" (command 22(n), index n of 0 to 255, electricity of 0.1×n (mA)), and "LIGHTENING TIME" (command 23(n), index n of 0 to 255, lightening time of 0.1×n (mSec)). "KIND OF LIGHT" is issued to specify the kind of light sources to be driven. "NUMBER OF LIGHT SOURCES TO BE LIGHTENED" is issued to specify the numbers of light sources to be lightened. "LIGHT AMOUNT" is issued to specify the light amount of the light source. "LIGHTENING TIME" is issued to specify lightening time of the light source.

The control command of the preset includes "CONDITION 0" (command 30, frame rate of 16 fps, lightening four short-range light sources 102), "CONDITION 1" (command 31, frame rate of 4 fps, lightening four short-range light sources 102 and two long-range light sources 103), and "CONDITION 2" (command 32, frame rate of 0.5 fps, lightening two short-range light sources 102 and two long-range light sources 103). "CONDITION 0" is suitable for shooting an image of the target region and its periphery. "CONDITION 1" is suitable for shooting an image of the region near the target region. "CONDITION 2" is suitable for shooting an image of the region away from the target region.

The other control command includes "CONTINUATION" (command 40), "TRANSMISSION POWER" (command 41(n), index n of 1 to 16, transmission power: P=n/16×Pmax, Pmax: maximum value of transmission power not over standard power), and the like. "CONTINUATION" is issued when the operation conditions have no change. "TRANSMISSION POWER" is issued to change the transmission power of the radio wave 14a. The CE judges the kind of control command by its number, and judges the setting of operation condition by its index.

Note that as shown in FIGS. 18 and 19, the value of frame rate and the number of light sources to be lightened are not limited to the above embodiment, and can be varied in accordance with the specification of the CE 11.

Here, there is fear that diagnostic information of patient other than the patient to be observed is downloaded to the receiver 12 by mistaken and endoscopy can not be performed correctly. In view of the above, it is necessary to certify whether the diagnostic information downloaded to the receiver 12 surely corresponds to the patient to be observed.

The method for certification is as follows, for example. The diagnostic information and a personal authentication ID for identifying each patient are stored in relation with each other. The personal authentication ID of the patient to be observed is registered in the CE before the endoscopy. When the diagnostic information is downloaded, the information of the personal authentication ID is also retrieved together with the diagnostic information to the receiver 12. Before starting the endoscopy, the information of the personal authentication ID is transmitted to the receiver 12 from the CE via the radio wave 14a. The personal authentication ID transmitted via the radio wave 14a and the personal authentication ID retrieved upon downloading the diagnostic information are checked in the receiver 12. Alternatively, in a case where the target region is not in an appropriate region as a result of the data analysis, the possibility in that the diagnostic information is downloaded by mistaken is high, and therefore the endoscopy may be halted by displaying warning or other methods.

Although common antennas and transmitting/receiving circuit are used to transmit/receive the image data and the control command in the above embodiment, separate antennas and separate transmitting/receiving circuit may be disposed for each of the image data and the control command.

Note that the methods for analyzing data, for producing the control command, for detecting the position, and respective components of the CE whose operation is controlled by the control command described in the above embodiment are only examples, and as long as they are within the scope of the present invention, any mode can be applied to the present invention.

The present invention is not to be limited to the above embodiments, and on the contrary, various modifications will be possible without departing from the scope and spirit of the present invention as specified in claims appended hereto.

What is claimed is:

1. A capsule endoscopic system composed of a capsule endoscope swallowed by a patient to be inspected for shooting an image of a region to be observed inside a body of said patient, a receiver for wirelessly receiving image data of said region to be observed obtained by said capsule endoscope and storing said image data, and an information management device for retrieving said image data of said region to be observed from said receiver to store and manage said image data, said capsule endoscopic system comprising:
   (A) said information management device includes:
      a first storage device for storing past diagnostic information of a past examination for said patient;
   (B) said receiver includes:
      a second storage device for storing said diagnostic information retrieved from said information management device;
      a first data analyzer for comparing first image data included in said diagnostic information and second image data included in present information obtained by said capsule endoscope during endoscopy to output an image feature value which shows extent of conformity between said first and second image data, and for comparing first position information included in said diagnostic information and second position information included in said present information to output a position evaluation value which shows extent of conformity between said first and second position information;

a control command producer for producing a control command to control operation of each component of said capsule endoscope based on an analysis result of said first data analyzer; and a wireless transmitter for wirelessly transmitting said control command; and (C) said capsule endoscope includes:

a wireless receiver for wirelessly receiving said control command; and an operation controller for causing each component of said capsule endoscope to operate in accordance with said control command, wherein said control command specifies a frame rate of said image shooting, wherein said frame rate is initially set at a first frame rate, wherein said frame rate is set at said first frame rate when said position evaluation value is less than a first threshold value, wherein said frame rate is set at said second frame rate when said position evaluation value is equal to or more than said first threshold value and said image feature value is less than a second threshold value, wherein said frame rate is set at a third frame rate higher than said second frame rate when said position evaluation value is equal to or more than said first threshold value and said image feature value is equal to or more than said second threshold value, wherein said frame rate is maintained at said second frame rate when said position evaluation value is less than said first threshold value, said image feature value is less than said second threshold value, said frame rate set last time is said second frame rate and a predetermined time has not elapsed since said frame rate was set at said second frame rate, and wherein said frame rate is set at said first frame rate when said position evaluation value is less than said first threshold value, said image feature value is less than said second threshold value, said frame rate set last time is said second frame rate and said predetermined time has elapsed since said frame rate was set at said second frame rate.

2. A capsule endoscopic system as defined in claim 1, wherein said control command is a release signal for performing said image shooting.

3. A capsule endoscopic system as defined in claim 1, wherein said control command switches said capsule endoscope between a first operation mode for performing said image shooting at a fixed arbitrary timing and a second operation mode for performing said image shooting at a second arbitrary timing.

4. A capsule endoscopic system as defined in claim 3, wherein
said image shooting is performed first and then said control command is produced based on image data obtained by said image shooting in said first operation mode, and
said control command is produced first and then said image shooting is performed in accordance with said control command in said second operation mode.

5. A capsule endoscopic system as defined in claim 1, wherein said control command switches said capsule endoscope to a third operation mode in which said image shooting is halted.

6. A capsule endoscopic system as defined in claim 1, wherein said control command specifies a driving condition of a light source section in said capsule endoscope.

7. A capsule endoscopic system as defined in claim 6, wherein said driving condition includes at least one of a kind of light sources constituting said light source section, a number of said light sources to be lightened, a light amount, and a lightening time.

8. A capsule endoscopic system as defined in claim 1, wherein said first image data is obtained at a periphery of a target region inside the body of said patient to be inspected.

9. A capsule endoscopic system as defined in claim 8, wherein said diagnostic information includes periphery position information at a periphery of said target region inside the body of said patient.

10. A capsule endoscopic system as defined in claim 9, wherein said periphery position information is stored in relation with said image data of said region to be observed.

11. A capsule endoscopic system as defined in claim 9, wherein said periphery position information includes at least one of a position of said capsule endoscope at the time of shooting an image at a periphery of said target region, operation time of said capsule endoscope, and a moving distance of said capsule endoscope.

12. A capsule endoscopic system as defined in claim 11, further comprising at least one of a position detector for detecting a position of said capsule endoscope, an operation time measurement device for measuring operation time of said capsule endoscope, and a moving distance measurement device for measuring a moving distance of said capsule endoscope, wherein at least one of a detection result of said position detector, a measurement result of said operation time measurement device, and a measurement result of said moving distance measurement device is used as said periphery position information.

13. A capsule endoscopic system as defined in claim 12, wherein said position detector includes an electric field strength detector for detecting an electric field strength of a wireless signal transmitted/received between said capsule endoscope and said receiver.

14. A capsule endoscopic system as defined in claim 12, wherein said operation time measurement device includes a clock circuit incorporated in said capsule endoscope or said receiver.

15. A capsule endoscopic system as defined in claim 12, wherein said moving distance measurement device includes an acceleration sensor for measuring acceleration of said capsule endoscope and an integrator for integrating said measurement result of said acceleration sensor.

16. A capsule endoscopic system as defined in claim 11, further comprising a pylorus passage detector for detecting that said capsule endoscope passes through a pylorus, wherein a point of time when said pylorus passage detector detects that said capsule endoscope passes through said pylorus is considered as a reference point of said operation time and said moving distance of said capsule endoscope.

17. A capsule endoscopic system as defined in claim 16, wherein said pylorus passage detector includes a pH sensor for measuring pH inside the body of said patient to be inspected.

18. A capsule endoscopic system as defined in claim 1, further comprising:
(A) said information management device includes:
a third storage device for storing case information obtained from a typical instance of disease; and
(B) said receiver includes:
a fourth storage device for storing said case information retrieved from said information management device; and
a second data analyzer for comparing said case information and said present information, wherein said control command producer produces said control command based on an analysis result of said second data analyzer.

19. A capsule endoscopic system as defined in claim 18, wherein said case information includes image data of at least one of a typical lesion and a foreign substance.

20. A capsule endoscopic system as defined in claim 1, wherein said capsule endoscope includes a fifth storage device for storing an operation condition of each component of said capsule endoscope set by said control command.

21. A capsule endoscopic system as defined in claim 1, wherein said wireless transmitter and said wireless receiver are used to wirelessly transmit/receive said image data of said region to be observed.

22. An operation control method of capsule endoscope comprising the steps of:

retrieving past diagnostic information of a past examination for a patient to be inspected from an information management device to a receiver;

comparing and analyzing first image data included in said diagnostic information and second image data included in present information obtained by a capsule endoscope during endoscopy to output an image feature value which shows extent of conformity between said first and second image data, and for comparing first position information included in said diagnostic information and second position information included in said present information to output a position evaluation value which shows extent of conformity between said first and second position information;

producing a control command to control operation of each component of said capsule endoscope based on an analysis result of said analyzing step;

wirelessly transmitting and receiving said control command between said receiver and said capsule endoscope; and causing each component of said capsule endoscope to operate in accordance with said control command, wherein said control command specifies a frame rate of said image shooting, wherein said frame rate is initially set at a first frame rate, wherein said frame rate is set at said first frame rate when said position evaluation value is less than a first threshold value, wherein said frame rate is set at said second frame rate when said position evaluation value is equal to or more than said first threshold value and said image feature value is than a second threshold value, wherein said frame rate is set at a third frame rate higher than said second frame rate when said position evaluation value is equal to or more than said first threshold value and said image feature value is equal to or more than said second threshold value, wherein said frame rate is maintained at said second frame rate when said position evaluation value is less than said first threshold value, said image feature value is less than said second threshold value, said frame rate set last time is said second frame rate and a predetermined time has not elapsed since said frame rate was set at said second frame rate, and wherein said frame rate is set at said first frame rate when said position evaluation value is less than said first threshold value, said image feature value is less than said second threshold value, said frame rate set last time is said second frame rate and said predetermined time has elapsed since said frame rate was set at said second frame rate.

* * * * *